(12) United States Patent
Popovic et al.

(10) Patent No.: US 9,592,380 B2
(45) Date of Patent: Mar. 14, 2017

(54) ELECTRICAL STIMULATION SYSTEM WITH PULSE CONTROL

(71) Applicant: MyndTec Inc., Mississauga (CA)

(72) Inventors: Milos Radomir Popovic, Mississauga (CA); Arkadiusz Biel, Toronto (CA); Harold Max Wodlinger, Vaughan (CA); Richard Fine, Mississauga (CA)

(73) Assignee: MyndTec Inc., Mississauga, Ontario (CA)

(*) Notice: Subject to any disclaimer, the term of this patent is extended or adjusted under 35 U.S.C. 154(b) by 0 days.

(21) Appl. No.: 14/775,581

(22) PCT Filed: Mar. 13, 2014

(86) PCT No.: PCT/CA2014/050236
§ 371 (c)(1),
(2) Date: Sep. 11, 2015

(87) PCT Pub. No.: WO2014/138990
PCT Pub. Date: Sep. 18, 2014

(65) Prior Publication Data
US 2016/0051817 A1 Feb. 25, 2016

Related U.S. Application Data

(60) Provisional application No. 61/791,805, filed on Mar. 15, 2013.

(51) Int. Cl.
*A61N 1/00* (2006.01)
*A61N 1/36* (2006.01)
(Continued)

(52) U.S. Cl.
CPC ..... *A61N 1/36014* (2013.01); *A61N 1/37247* (2013.01); *G06Q 50/22* (2013.01); *G06Q 50/24* (2013.01)

(58) Field of Classification Search
CPC ............ A61N 1/36021; A61N 1/36014; A61N 1/36067; A61N 1/36082; A61N 1/36135; A61N 1/36153
See application file for complete search history.

(56) References Cited

U.S. PATENT DOCUMENTS 4,875,484 A 10/1989 Anzai et al.
5,514,165 A 5/1996 Malaugh et al.
(Continued)

FOREIGN PATENT DOCUMENTS

CA 2801333 12/2011
CN 101869739 A 10/2010
(Continued)

OTHER PUBLICATIONS

Tarulli et al., A Multi-Channel Current-Regulated Output Stage for an Electrical Stimulator, Rehabilitation Engineering Laboratory; Institute of Biomaterials and Biomedical Engineering, University of Toronto, Toronto Rehabilitation Institute, Undated, 1 page.
(Continued)

*Primary Examiner* — Robert N Wieland
(74) *Attorney, Agent, or Firm* — Bret E. Field; Bozicevic, Field & Francis LLP

(57) ABSTRACT

An electrical stimulation system to provide pulse stimulation to an area of a living body by way of one or more electrode leads applied to the area, the area including an associated resistance element and an associated capacitance element. The system may include a pulse generating circuit having a controllable output voltage to generate constant voltage pulses to the one or more electrode leads, wherein the corresponding current signal of each constant voltage pulse includes an exponential decay to a steady state current value. The system may include a controller configured to estimate the associated resistance element of the area, determine a specified target steady state current value to be applied to the
(Continued)

area, and control the pulse generating circuit to generate a constant voltage pulse to the one or more electrode leads at a calculated voltage level which achieves the specified target steady state current value to the area.

21 Claims, 31 Drawing Sheets

(51) Int. Cl.
  *G06Q 50/22* (2012.01)
  *G06Q 50/24* (2012.01)
  *A61N 1/372* (2006.01)

(56) References Cited

U.S. PATENT DOCUMENTS

| | | | |
|---|---|---|---|
| 6,167,301 | A | 12/2000 | Flower et al. |
| 6,810,286 | B2 | 10/2004 | Donovan et al. |
| 7,180,760 | B2 | 2/2007 | Varrichio et al. |
| 7,317,948 | B1 | 1/2008 | King et al. |
| 7,359,751 | B1 | 4/2008 | Erickson et al. |
| 8,014,866 | B2 | 9/2011 | Haefner |
| 8,086,310 | B2 | 12/2011 | Armstrong et al. |
| 8,108,049 | B2 | 1/2012 | King |
| 8,121,702 | B2 | 2/2012 | King |
| 8,155,740 | B2 | 4/2012 | Wanasek |
| 8,209,005 | B1 | 6/2012 | Moulder et al. |
| 8,311,639 | B2 | 11/2012 | Parker et al. |
| 2004/0015203 | A1* | 1/2004 | McGraw ............. A61N 1/326 607/48 |
| 2009/0112292 | A1 | 4/2009 | Armstrong |
| 2010/0324626 | A1 | 12/2010 | Lefkovitz |
| 2011/0066209 | A1 | 3/2011 | Bodlaender et al. |
| 2011/0093041 | A1 | 4/2011 | Straka et al. |
| 2011/0264171 | A1 | 10/2011 | Torgerson |
| 2013/0006324 | A1 | 1/2013 | Bradley |

FOREIGN PATENT DOCUMENTS

| | | |
|---|---|---|
| GB | 1435996 | 5/1976 |
| WO | WO0119452 | 3/2001 |
| WO | WO2010069317 | 6/2010 |
| WO | WO2011150502 | 12/2011 |

OTHER PUBLICATIONS

International Search Report and Written Opinion for PCT Patent Application No. PCT/CA2014/050236 dated Jun. 11, 2015, 13 pages.

Merrill et al., Electrical stimulation of excitable tissue: design of efficacious and safe protocols; Journal of Neuroscience Methods 141 (2005) 171-198.

Unity Network, Patient Data Server (PDS) Operators Manual; Software Version 1, 2016777-001 Revision A; GE Medical Systems Information Technologies; 2003, 54 pages.

* cited by examiner

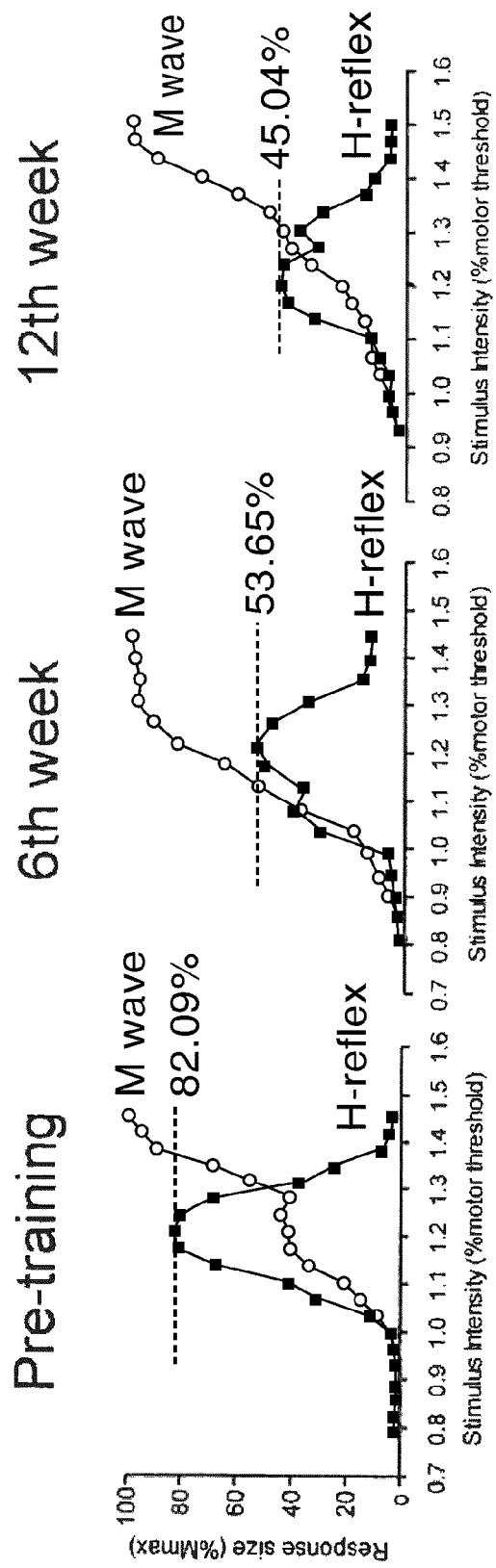
FIG. 17
FIG. 18
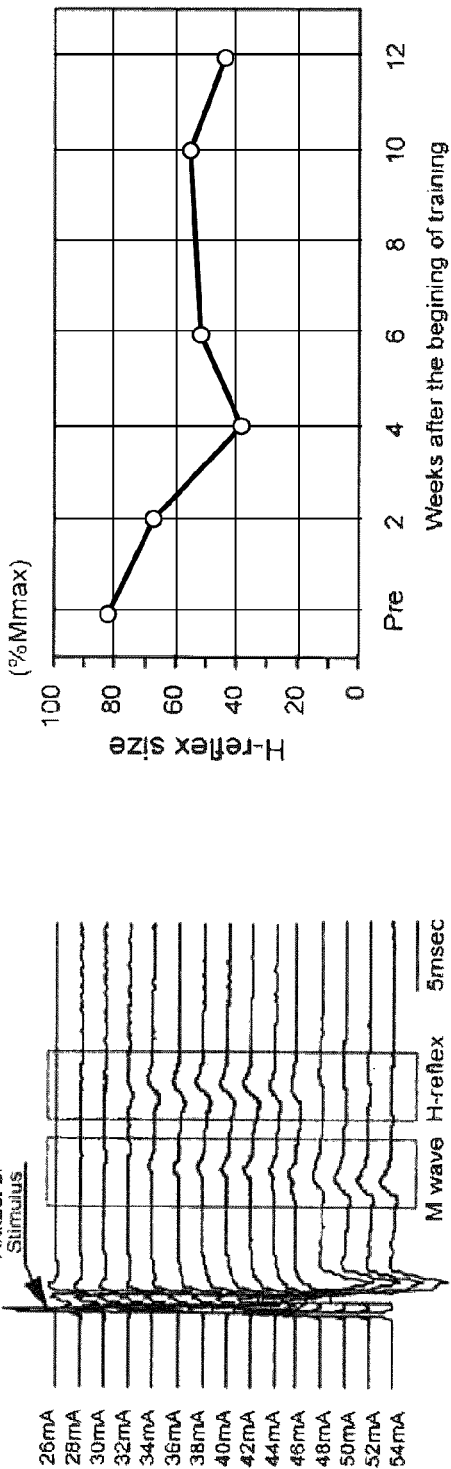
FIG. 19

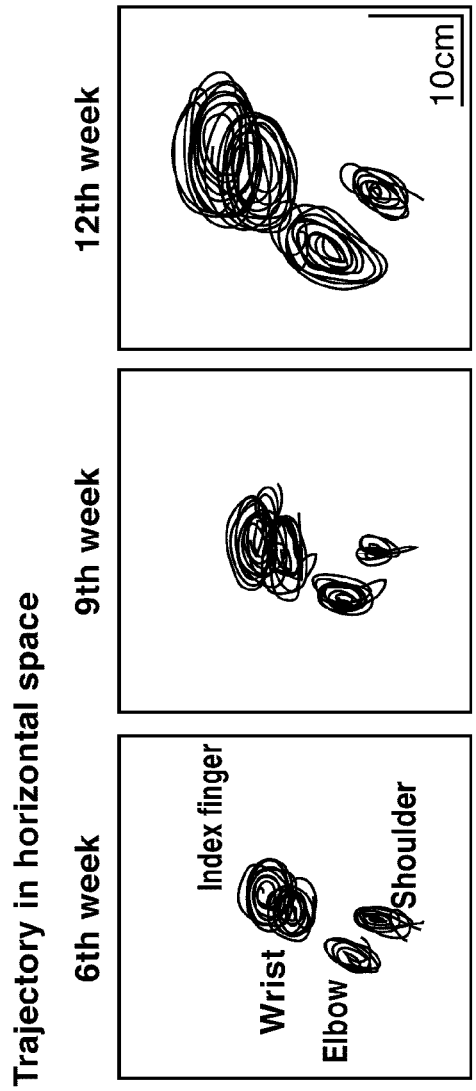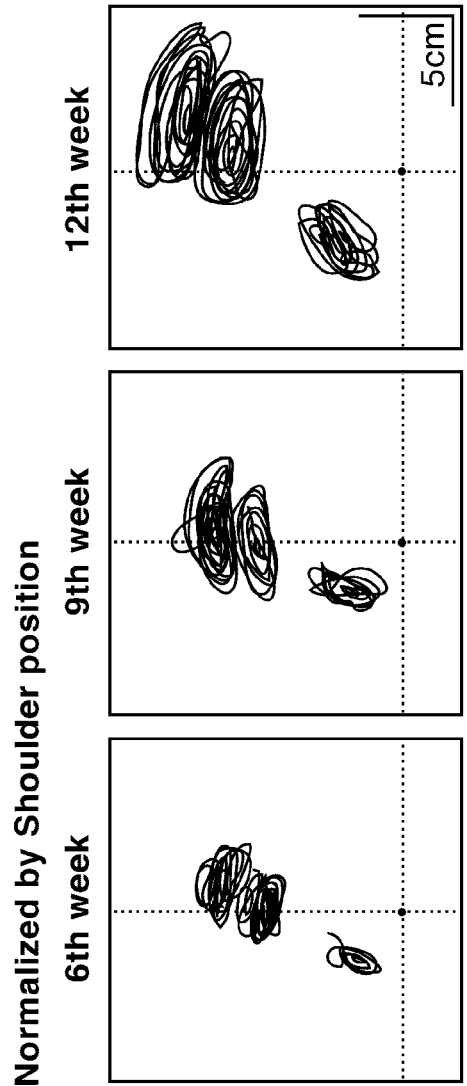
FIG. 21
FIG. 22

ELECTRICAL STIMULATION SYSTEM WITH PULSE CONTROL

CROSS-REFERENCE TO RELATED APPLICATIONS

This application claims the benefit of priority to U.S. Patent Application No. 61/791,805 filed Mar. 15, 2013, the contents of which are herein incorporated by reference.

FIELD OF THE DISCLOSURE

The present disclosure relates to electrical stimulation, and for example, to a functional electrical stimulation device and system.

BACKGROUND

The general principles of functional electrical stimulation (FES) are rooted in the physiological process of nerve and muscle excitation. These excitations are a result of action potentials (APs) that occur in the body at the neuronal and muscular levels. APs are the messenger signals for the neuromuscular system. They occur in muscle and nervous system tissues in response to stimuli, which can be natural or artificial. In the case of FES, these stimuli are charge pulses. Depending on the amplitude, duration and frequency of these stimuli they can cause excitation in different tissues. FES therapies use these excitation pulses to treat patients with impairments in different areas of the body. Owing to the complexity of generating APs, the artificial electrical stimulation pulses which can generate these APs may require particular pulse types and stimulation schemes for FES applications.

All body cells display a membrane potential, which is a separation of positive and negative charges across the membrane. This potential is related to the uneven distribution of potassium ions (K+ ions), sodium ions (Na+ ions) and large intracellular protein anions between the intracellular and extracellular fluid and to the differential permeability of the plasma membrane to these ions and to activate ion pump mechanisms.

Two types of cells, muscle cells and nerve cells, have developed specialized use for this membrane potential. Nerve and muscle are excitable tissues that produce action potentials when their resting potentials change through excitation or other biological processes. Action potentials allow nerve and muscle cells to communicate. FES uses artificial stimuli in the form of electrical pulses to elicit excitation in different tissues.

Neuromuscular electrical stimulation (NMES) is one of the useful therapeutic methods to improve motor function. Studies examining the use of NMES have demonstrated improvements in joint range of motion, force and torque production, magnitude of electromyographic (EMG) muscular activity, and muscle tone. Functional electrical stimulation (FES) is a device-mediated therapy that integrates electrical stimulation of sensory-motor systems and repetitive functional movement of the paretic limb or a body part or a body function in patients with different forms of neuromuscular disorder, such as stroke, spinal cord injury, multiple sclerosis, cerebral palsy, and traumatic brain injury, to name a few.

Some known FES devices, although useful, have had limited success at reaching their full potential. For example, some previous devices have not been able to ensure charge balance over time because of partial control over temporal characteristics and amplitude. They also provide a limited number of pulses and require complicated and costly adjustments for use in different FES applications.

Nonetheless, various functional electrical stimulators have been used over time to improve the lives of patients with various neurological and musculoskeletal disorders and muscular atrophies as well as in therapy for sport injuries. Known FES devices provide electrical pulses activating a single or a group of muscles, to create a movement (neuroprosthetic applications) and/or build up the muscle mass (neuromuscular stimulation applications). FES devices have also been used in treating bladder problems, easing the symptoms of Parkinson's disease and numerous other applications. Generally, for each application a specific FES system is used.

Some existing known stimulators typically produce either voltage or current regulated electrical pulses. Current regulated pulses generally deliver the same amount of charge to the tissue regardless of tissue resistance. However, some existing systems, which regulate current, have very slow voltage rise times, which can lead to high steady state current, leading to discomfort.

Other difficulties may be appreciated in view of the detailed description below.

SUMMARY

It is recognized herein that stimulating with a very fast voltage rise time (e.g. 10 to 20 ns) results in significantly less steady-state current required to achieve the same stimulation. It is recognized herein that a fast rise time may assist to reduce the stimulation intensity applied to the patient.

At least some example embodiments relate to a functional electrical stimulation (FES) system and associated methods. The system provides pulse stimulation to an area of a living body by way of one or more electrode leads applied to the area, the area including an associated resistance element and an associated capacitance element. The system may include a pulse generating circuit having a controllable output voltage to generate constant voltage pulses to the one or more electrode leads, wherein the corresponding current signal of each constant voltage pulse includes an exponential decay to a steady state current value. The system includes a controller configured to estimate the associated resistance element of the area, determine a specified target steady state current value to be applied to the area, and control the pulse generating circuit to generate a constant voltage pulse to the one or more electrode leads at a calculated voltage level which achieves the specified target steady state current value to the area.

In accordance with an example embodiment, there is provided a method for controlling an electrical stimulation system for providing pulse stimulation to an area of a living body by way of one or more electrode leads applied to the area, the area including an associated resistance element and an associated capacitance element, wherein the electrical stimulation system includes a pulse generating circuit having a controllable output voltage to generate constant voltage pulses to the one or more electrode leads, wherein the corresponding current signal of each constant voltage pulse includes an exponential decay to a steady state current value. The method includes estimating the associated resistance element of the area, determining a specified target steady state current value to be applied to the area, and controlling the pulse generating circuit to generate a constant voltage pulse to the one or more electrode leads at a calculated voltage level which achieves the specified target steady state current value to the area.

In accordance with another example embodiment, there is provided a controller for controlling an electrical stimulation system for providing pulse stimulation to an area of a living body by way of one or more electrode leads applied to the area, the area including an associated resistance element and an associated capacitance element, wherein the electrical stimulation system includes a pulse generating circuit having a controllable output voltage to generate constant voltage pulses to the one or more electrode leads, wherein the corresponding current signal of each constant voltage pulse includes an exponential decay to a steady state current value. The controller is configured to estimate the associated resistance element of the area, determine a specified target steady state current value to be applied to the area, and control the pulse generating circuit to generate a constant voltage pulse to the one or more electrode leads at a calculated voltage level which achieves the specified target steady state current value to the area.

In accordance with yet another example embodiment, there is provided a non-transitory computer readable medium having instructions stored thereon executable by a controller for controlling an electrical stimulation system for providing pulse stimulation to an area of a living body by way of one or more electrode leads applied to the area, the area including an associated resistance element and an associated capacitance element, wherein the electrical stimulation system includes a pulse generating circuit having a controllable output voltage to generate constant voltage pulses to the one or more electrode leads, wherein the corresponding current signal of each constant voltage pulse includes an exponential decay to a steady state current value. The instructions include instructions for estimating the associated resistance element of the area, determining a specified target steady state current value to be applied to the area, and instructions for controlling the pulse generating circuit to generate a constant voltage pulse to the one or more electrode leads at a calculated voltage level which achieves the specified target steady state current value to the area.

In accordance with yet another example embodiment, there is provided a tablet computer for controlling a processor board which provides pulse stimulation to an area of a living body by way of one or more electrode leads applied to the area, the area including an associated resistance element and an associated capacitance element, wherein the processor board controls a pulse generating circuit having a controllable output voltage to generate constant voltage pulses to the area, wherein the corresponding current signal of each constant voltage pulse includes an exponential decay to a steady state current value, The tablet computer includes: a touchscreen for displaying a user interface which at least displays an option to activate the pulse generating circuit; and a controller configured to estimate the associated resistance element of the area, determine a specified target steady state current value to be applied to the area, and control the pulse generating circuit, through the processor board, to generate a constant voltage pulse to the one or more electrode leads at a calculated voltage level which achieves the specified target steady state current value to the area.

In accordance with yet another example embodiment, there is provided a computer device for managing patient information in relation to electrical stimulation therapy by way of pulses applied to a patient, the device including: an interface for receiving information in relation to the electrical stimulation therapy, the information including detected information of the pulses applied to the patient; a memory for storing the received information; and a communications subsystem for communicating the received information to a remote server.

In accordance with yet another example embodiment, there is provided a method of prescribing a treatment to a patient, including: receiving a prescription purchase request; and providing a patient dedicated electronic key in response to the purchase request, wherein the electronic key comprises at least one or all of: a. access to protocol(s) for a prescribed therapy intervention, b. a record of the pattern of use of the protocols, including at least duration, frequency and amplitude of pulses to be applied to the patient, c. outcomes captured during treatment, and d. reports on progress and treatment planning.

In accordance with yet another example embodiment, there is provided a computer device for controlling an electrical stimulation system for providing pulse stimulation to a patient, including: a display screen which displays a graphical user interface (GUI), the GUI being configured to receive user inputs in relation to the pulse stimulation for at least one of: a. protocols, b. diagnostics that report patient progress, and c. instructional material including videos, help menus or user manual.

In accordance with yet another example embodiment, there is provided an electrical stimulation system for providing pulse stimulation to a plurality of areas of a living body by way of a plurality of electrode leads each applied to one of the respective areas, each of the areas including an associated resistance element and an associated capacitance element, at least two of the plurality of areas are of a distance which causes biological cross-talk between respective electrode leads, the system including: a plurality of pulse generating circuits each having a controllable output voltage to generate constant voltage pulses to one or more of the electrode leads, wherein the corresponding current signal of each constant voltage pulse includes an exponential decay to a steady state current value; and at least one controller is configured to: estimate the associated resistance element of each area, control the pulse generating circuits to generate a constant voltage pulse to each of the electrode leads at a specified voltage level based on the measured steady-state current value, and control a spike of one of the current signals for one of the electrode leads so as to be outside the steady-state current of another one of the electrode leads to allow accurate measurement of the steady-state current of the another one of the electrode leads.

Other aims, objects, advantages and features of the example embodiments, and/or difficulties with existing conventional systems, will become more apparent upon reading of the following non-restrictive description of specific embodiments thereof, given by way of example only with reference to the accompanying drawings.

BRIEF DESCRIPTION OF THE FIGURES

Example embodiments of the present disclosure will be provided, by way of examples only, with reference to the appended drawings, in which:

FIG. 17 is a graph of recruitment curves of H-reflex and M wave obtained in pre-training and at various time points;

FIG. 18 is a graph of exemplary elicited M wave and H-reflex curves;

FIG. 19 is a graph of changes of H-reflex and M response curves with time course of training;

FIG. 21 is an exemplary x-y plot of the absolute positions of the shoulder, elbow, wrist joint, and index finger position during a circle drawing test;

FIG. 22 is an exemplary x-y plot of the positions of the elbow, wrist joint, and index finger position during a circle drawing test normalized to the shoulder position;

FIG. 25 is an example user interface screen displayed on a computer device for patient treatment, in accordance with an example embodiment;

FIG. 26 is an example user interface screen displayed on a computer device for session details, in accordance with an example embodiment;

Like reference numerals may be used throughout the Figures to denote similar elements and features.

DETAILED DESCRIPTION OF EXAMPLE EMBODIMENTS

With reference to the disclosure herein and the appended figures, a functional electrical stimulation (FES) device and system, and use thereof will now be described, in accordance with different example embodiments.

Figure 1:
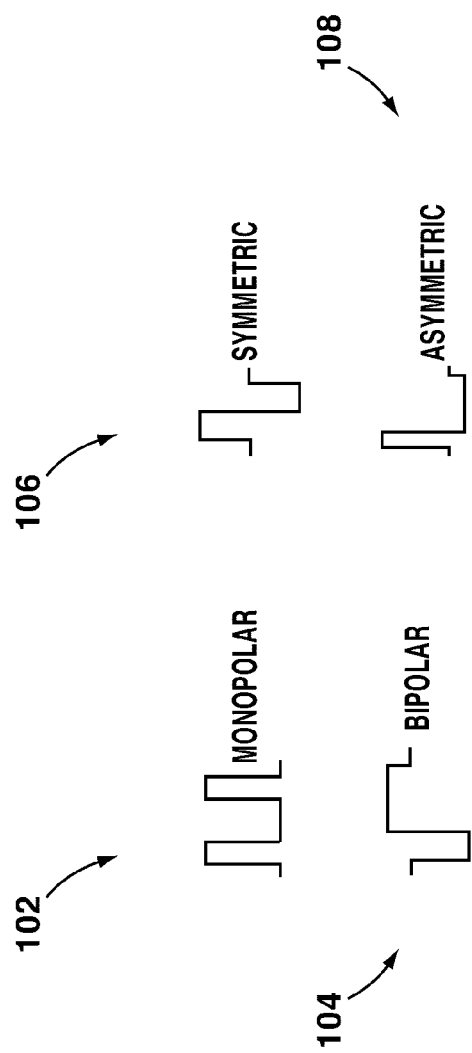
FIG. 1 is a schematic representation of various pulse characteristics applicable in different FES applications, a selection of one or more of which being available through implementation of different example embodiments.

FIG. 1 shows common classifications of pulse shapes that can be used in FES applications. A monopolar or unipolar pulse sequence 102 includes pulses from a reference state such as ground to and from a positive state only, as shown, or alternatively a negative state only. A bipolar pulse sequence 104 includes pulses which are both positive and negative from the reference state. A symmetric pulse sequence 106 includes consecutive pulses which have equal and opposite amplitudes. An asymmetric pulse sequence 108 includes consecutive pulses which may have unequal opposite amplitudes. The pulse shapes can represent voltage or current, depending on the particular application. A parameter of interest in FES applications, particularly where bipolar pulses are used, is that the net electric charge brought by each pulse be as close to zero as possible, which parameter generally applies in the application of symmetric and asymmetric bipolar pulses. This feature is generally considered relevant in preventing or at least reducing charge accumulation in the tissue, which may cause a galvanic process that may lead to tissue breakdown, for example.

Figure 7:
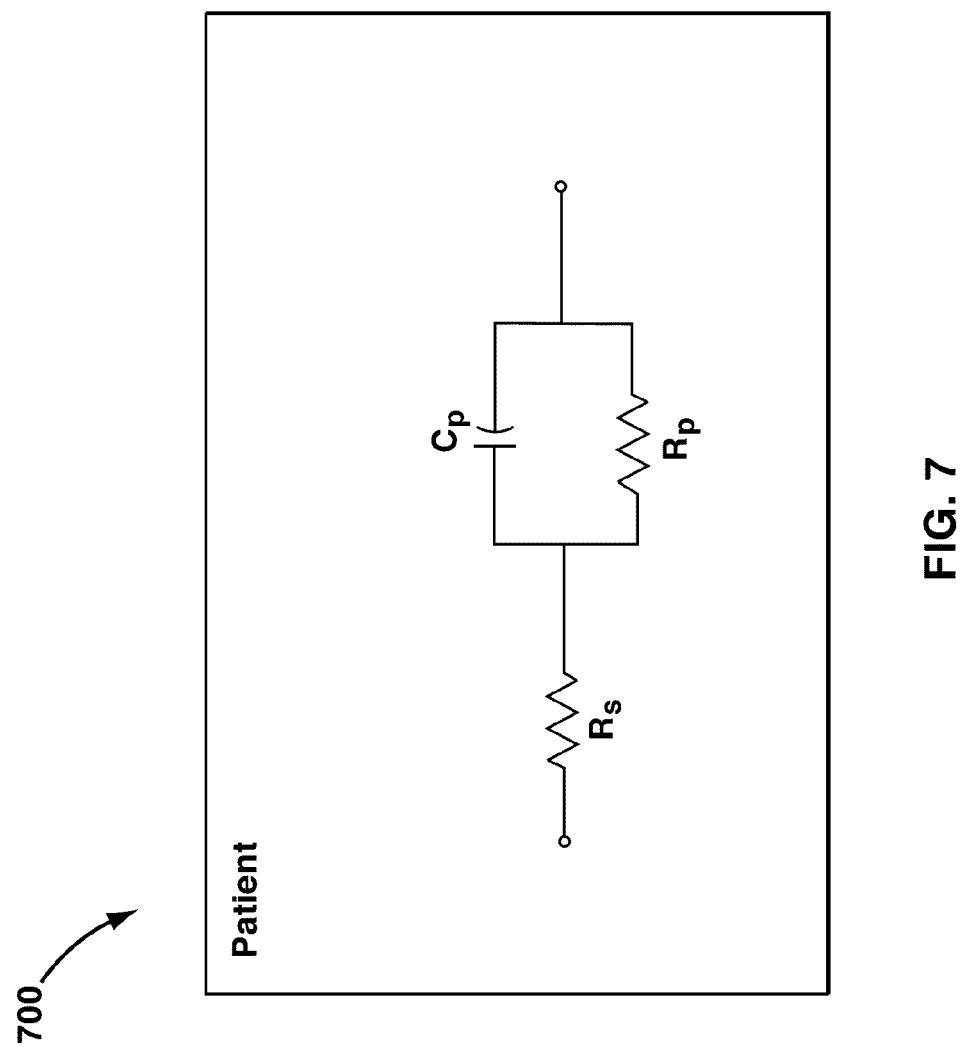
FIG. 7 is an example schematic representation of an equivalent circuit model for skin impedance of a patient, to which example embodiments can be applied.

Reference is now made to FIG. 7, which is an example schematic representation of an equivalent circuit model 700 for impedance of an area or region of a patient 700 such as the skin, to which example embodiments can be applied. The area of the patient 700 can be represented by at least an associated resistance element and an associated capacitance element. In the example shown, the equivalent circuit model 700 includes a series resistance (Rs) and, in parallel, a capacitor (Cp) and a resistor (Rp). Other more complex models may be used in other example embodiments, which may include further resistance elements and/or further capacitance elements. For example, the electrode interface, skin, spreading resistance, and body resistance, may further add resistance elements and capacitance elements, as understood in the art, which may be used depending on the desired model complexity. The resistance elements and the capacitance elements of the patient can change over time, for example based on physiological changes or as a response to the present FES treatment (which can be e.g. 5 seconds). For example, note that skin characteristics of resistance and capacitance can be significantly affected by variable factors such as moisturizers. For the model 700, the associated total resistance of the patient area can be represented by, for example, Rs+Rp.

By measuring patient's skin resistance at different skin points (where the stimulation is delivered), example embodiments of the present FES systems can be used to create patients "resistance signature". For example, this means that if somebody tries to use the protocols assigned to subject A we can determine when somebody tried to apply it to subject B. The patient's skin "resistance signature" and the stimulation amplitudes (e.g. change in the amplitudes coupled with different "resistance signature") can be used to determine fraud or an attempt to use protocols assigned for one person (person A) with another person (person B).

Figure 8:
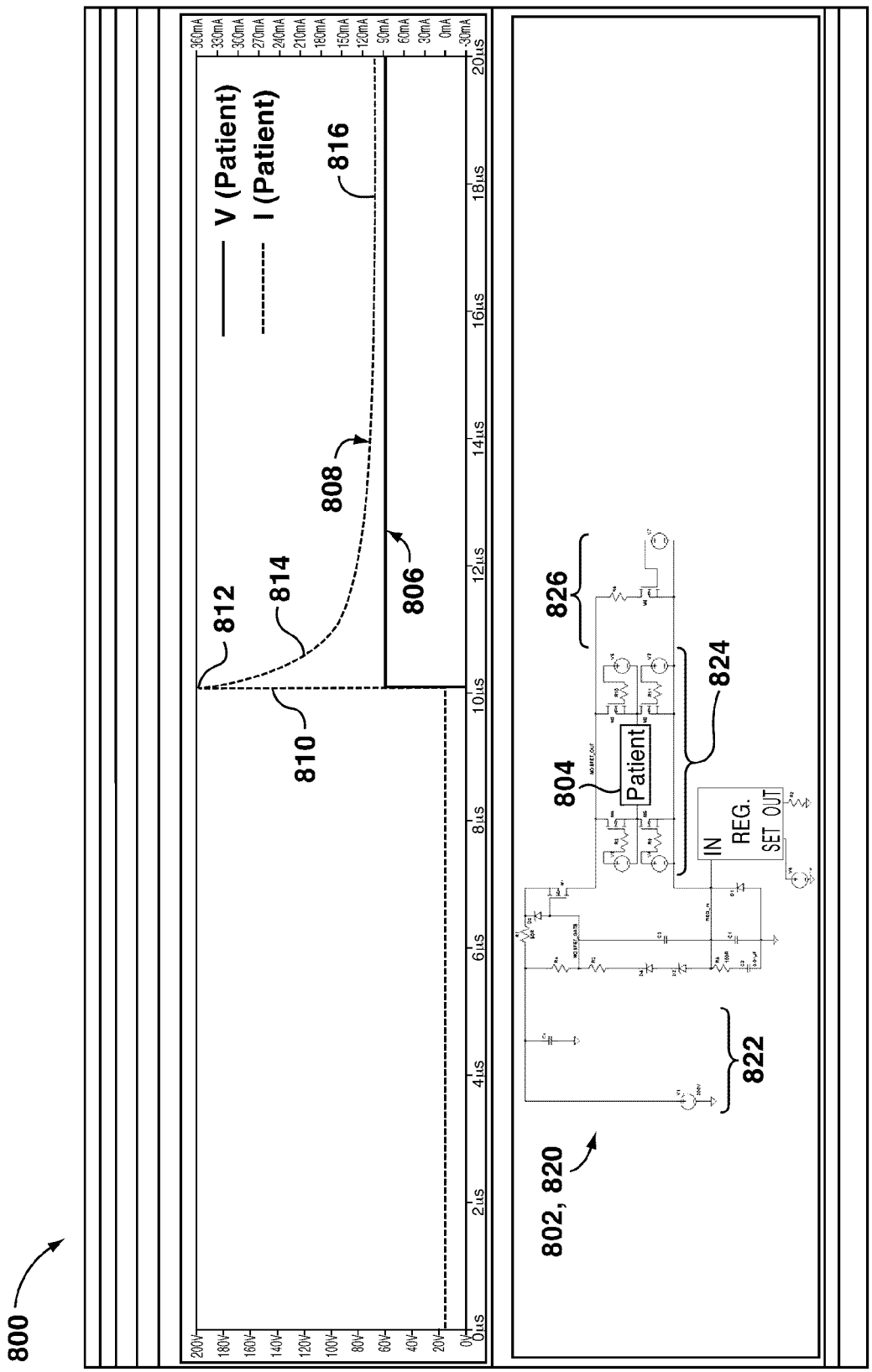
FIG. 8 illustrates a plot and schematic diagram of a signal pulse applied to the patient, in accordance with an example embodiment.

An example controlled pulse is best illustrated in FIG. 8, which shows a plot 800 and associated schematic diagram of a signal pulse applied to the patient 804, in accordance with an example embodiment. The patient 804 may have a steady state resistance value of 600 Ohms, for example. Generally, in accordance with at least some example embodiments, there is provided a functional electrical stimulation (FES) system 802 for providing pulse stimulation to an area of the patient 804 by way of one or more electrode leads applied to the area. The FES system 802 includes a pulse generating circuit 820 having a controllable output voltage to generate rectangular or near-rectangular constant voltage pulses 806 to the one or more electrodes. The rising edge of the voltage pulses 806 have a high slew rate. Because the capacitance element of the patient area (e.g. as illustrated FIG. 7) can be relatively large, the corresponding current signal profile 808 of each constant voltage pulse 806 includes an initial inrush of current 810 having a high slew rate, which then achieves a peak or spike 812. The spike 812 is followed by an exponential decay 814 to a steady state current value 816. This type of current response can also be referred to as a voltage step response, for example. The system 802 can receive instructions or input from a practitioner regarding the specified target steady state current value 816 to be applied to the area, which is the desired charge dosage to the patient 804. The voltage of the constant voltage pulse 806 is a calculated voltage level which achieves the specified target steady state current value to the area. For example, Ohms' Law (V=R*I) can be used to calculate the required voltage level, dependent on the present resistance element of the patient area 804 and the specified target steady state current value. The present resistance element of the patient 804 can be determined in a number of ways, in accordance with example embodiments, as described in detail herein.

For each subsequent pulse, the calculated constant voltage level of the voltage pulse 806 is adjusted to achieve the specified target steady state current (due to possible changes in patient resistance element). This voltage adjustment is made by measuring the current that is actually delivered by the target voltage, determining the present electrical resistance element, and then adjusting the target voltage level. The practitioner or user specifies the stimulation in terms of steady state current, so that the system delivers a consistent desired charge regardless of the resistance element of the patient.

Accordingly, for each pulse the voltage is regulated to a voltage level defined by a specified target steady-state current of the patient 804, so that switch activation of each pulse provides an initial inrush of current at the voltage level, and wherein the resultant current achieves the specified target steady-state current value. It is recognized herein that stimulating with a very fast voltage rise time (e.g. 10 to 20 ns) results in significantly less steady-state current required to achieve the same stimulation. Note that, the example embodiments use constant voltage pulses which are in contrast to, and not the same as, a pulse generator which merely generates a rectangular constant current pulse.

In the example circuit 820 shown in FIG. 8, the pulse generating circuit 820 can include at least a controllable constant voltage source 822 and a switching circuit 824 which includes, for example, switches in an H-bridge configuration. An alternate path 826 is also shown, which allows selective drainage of charge which is alternate from the switching circuit 824.

Figure 9:
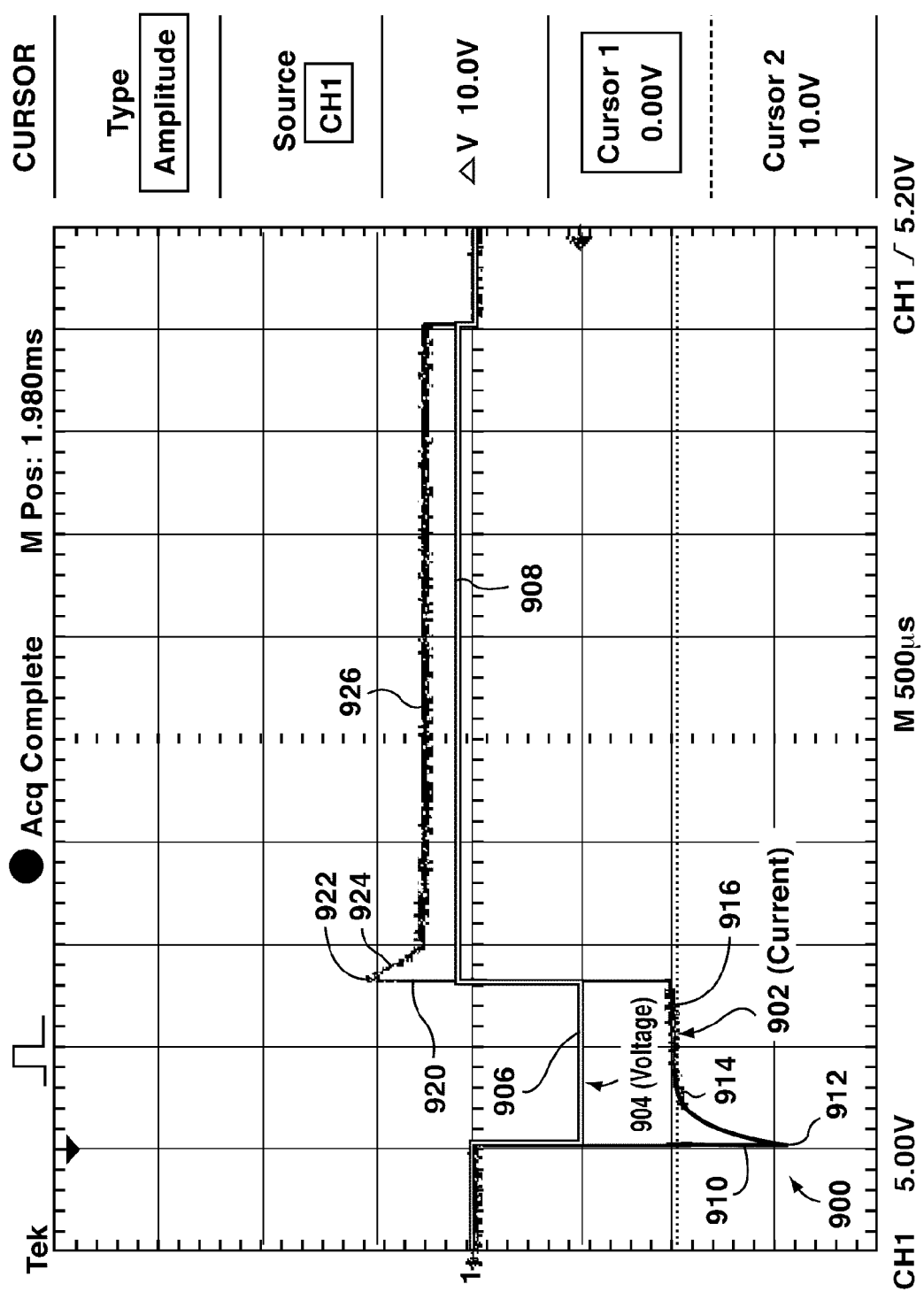
FIG. 9 is a plot of an asymmetrical pulse sequence applied the patient, in accordance with an example embodiment.
Figure 10:
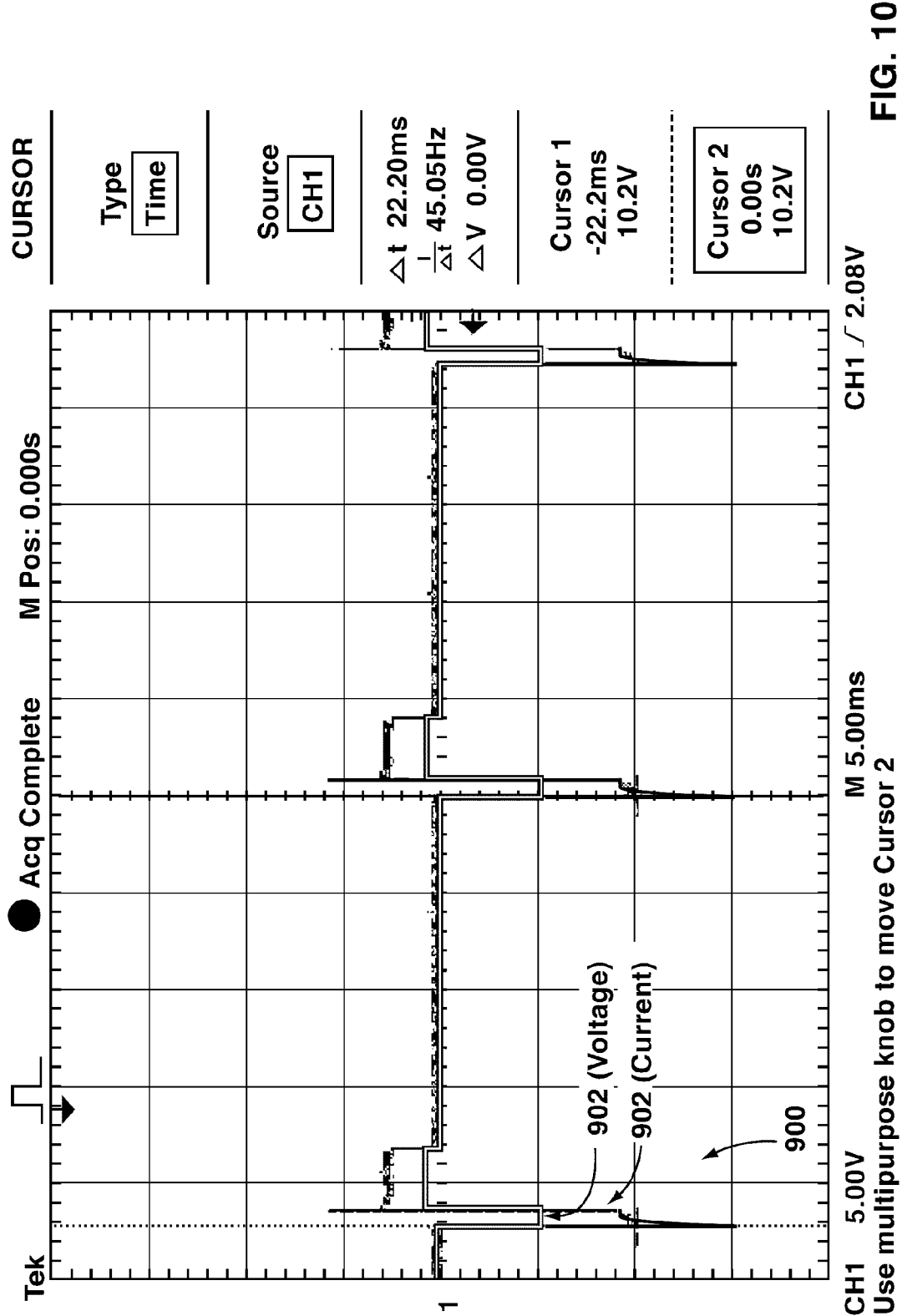
FIG. 10 is a plot which illustrates the asymmetrical pulse sequence of FIG. 9 as a pulse train, in accordance with an example embodiment.

Reference is now made to FIGS. 9 and 10, which illustrate a plot of an asymmetrical pulse sequence 900 applied to the patient, in accordance with an example embodiment. FIG. 10 is the pulse sequence 900 applied as a pulse train having a specified frequency. In an example embodiment, the illustrated pulse sequences are a result of the one or more cathodes being places on the stimulation target site(s) on the body, while the anode is placed at another suitable site to complete a nerve stimulation path. In the examples shown, each pulse sequence can include a negative pulse followed by a positive pulse, wherein the positive pulse is one quarter of the amplitude of the negative pulse, and has a pulse width that is four times that of the negative pulse. This allows the charge across the patient area to be balanced. Other example asymmetric pulses may have different amplitude and pulse width ratios, wherein net charge is balanced (e.g. equal or close to zero).

Referring to FIG. 9, the asymmetrical pulse sequence 900 illustrates the current pulse sequence 902 and the voltage pulse sequence 904 as applied to the patient. At the negative pulse of the voltage pulse sequence 904, the voltage applied is set to a constant negative voltage level 906 (e.g. −V). The voltage level 906 is calculated in dependence of the desired target steady state current value and the presently known value of the resistance element of the patient. At the positive pulse of the voltage pulse sequence 904, the voltage is applied as a constant positive voltage level 908 which is one quarter of the negative voltage level (e.g. ¼V) and four times the pulse width of the negative pulse.

At the negative pulse of the current sequence 902, the current pulse includes an initial inrush of current 910 having a high slew rate, which then achieves a peak or spike 912. The spike 912 is followed by an exponential decay 914 to a steady state current value 916. Typically, the practitioner defines the parameters of the desired pulse sequence 902 by specifying the target steady state current value 916, and the voltage level 906 is controlled to achieve that steady state current value 916.

At the positive pulse of the current sequence 902, the current pulse includes an inrush of current 920 having a high slew rate, which then achieves a peak or spike 922. The spike 922 is followed by an exponential decay 924 to a steady state current 924.

Figure 11:
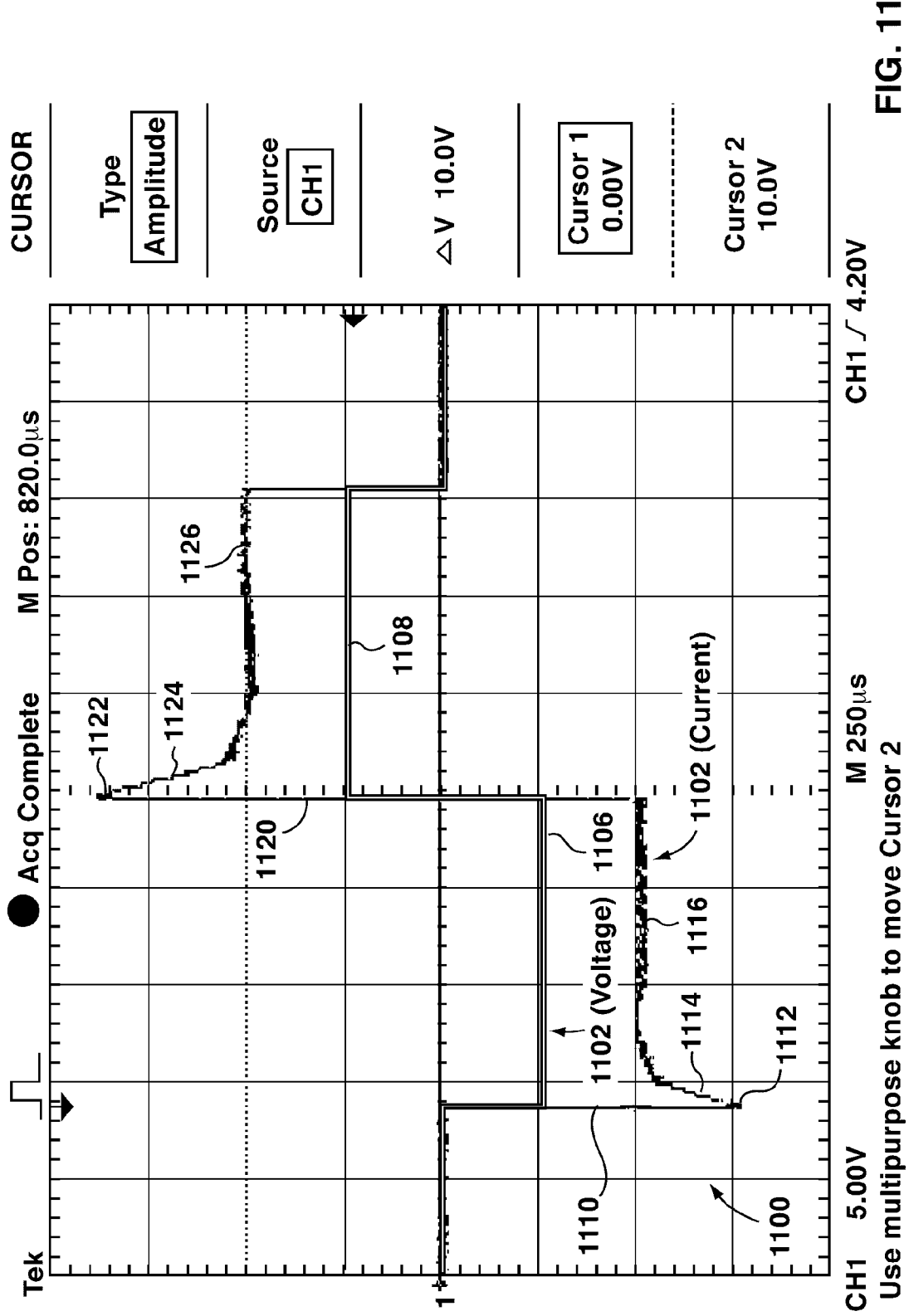
FIG. 11 is a plot of a symmetrical pulse sequence applied to the patient, in accordance with an example embodiment.
Figure 12:
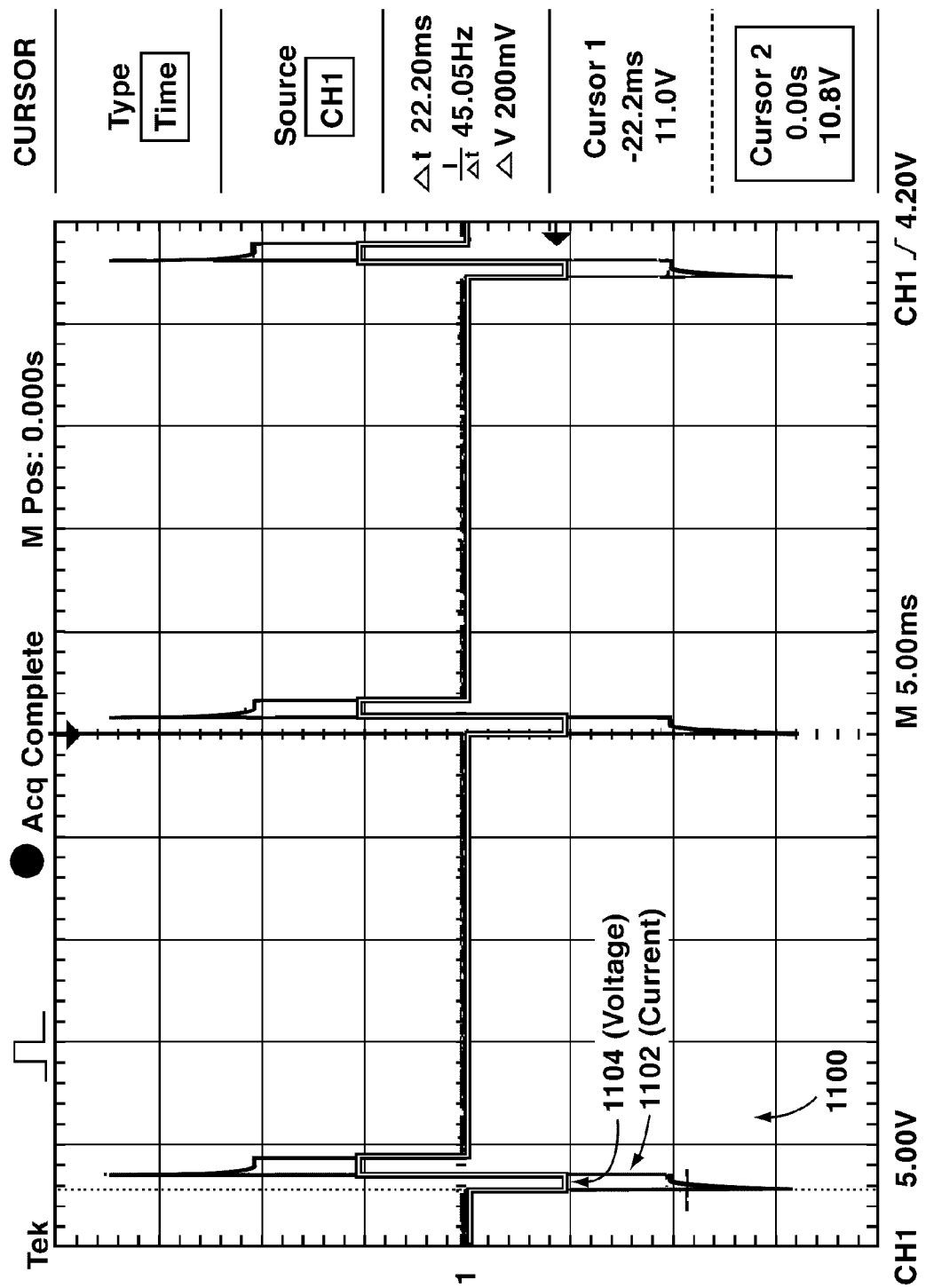
FIG. 12 is a plot which illustrates the symmetrical pulse sequence of FIG. 11 as a pulse train, in accordance with an example embodiment.

Reference is now made to FIGS. 11 and 12, which illustrate a plot of a symmetrical pulse sequence 1100 applied to the patient, in accordance with an example embodiment. FIG. 12 is the pulse sequence 1100 applied as a pulse train having a specified frequency. For example, the illustrated pulse sequences are a result of the one or more cathodes being places on the stimulation target site(s) on the body, while the anode is placed at another suitable site to complete a nerve stimulation path. In the example shown, each pulse sequence can include a negative pulse and a positive pulse which have equal and opposite amplitudes, and which have equal pulse widths. This allows the charge across the patient area to be balanced.

Referring to FIG. 11, the asymmetrical pulse sequence 1100 illustrates the current pulse sequence 1102 and the voltage pulse sequence 1104 as applied to the patient. At the negative pulse of the voltage pulse sequence 1104, the voltage applied is set to a constant negative voltage level 1106 (e.g. −V). The voltage level 1106 is calculated in dependence of the desired target steady state current value and the presently known value of the resistance element of the patient. At the positive pulse of the voltage pulse sequence 1104, the voltage is applied as a constant positive voltage level 1108 having the same amplitude as the negative voltage level (e.g. +V).

At the negative pulse of the current sequence 1102, referring still to FIG. 11, the current pulse includes an initial inrush of current 1110 having a high slew rate, which then achieves a peak or spike 1112. The spike 1112 is followed by an exponential decay 1114 to a steady state current value 1116. Typically, the practitioner defines the parameters of the desired pulse sequence 1102 by specifying the target steady state current value 1116, and the voltage level 1106 is controlled by the processor 408 (FIG. 4) to achieve that steady state current value 1116.

At the positive pulse of the current sequence 1102, referring still to FIG. 11, the current pulse includes an inrush of current 1120 having a high slew rate, which then achieves a peak or spike 1122. The spike 1122 is followed by an exponential decay 1124 to a steady state current 1124.

Figure 2:
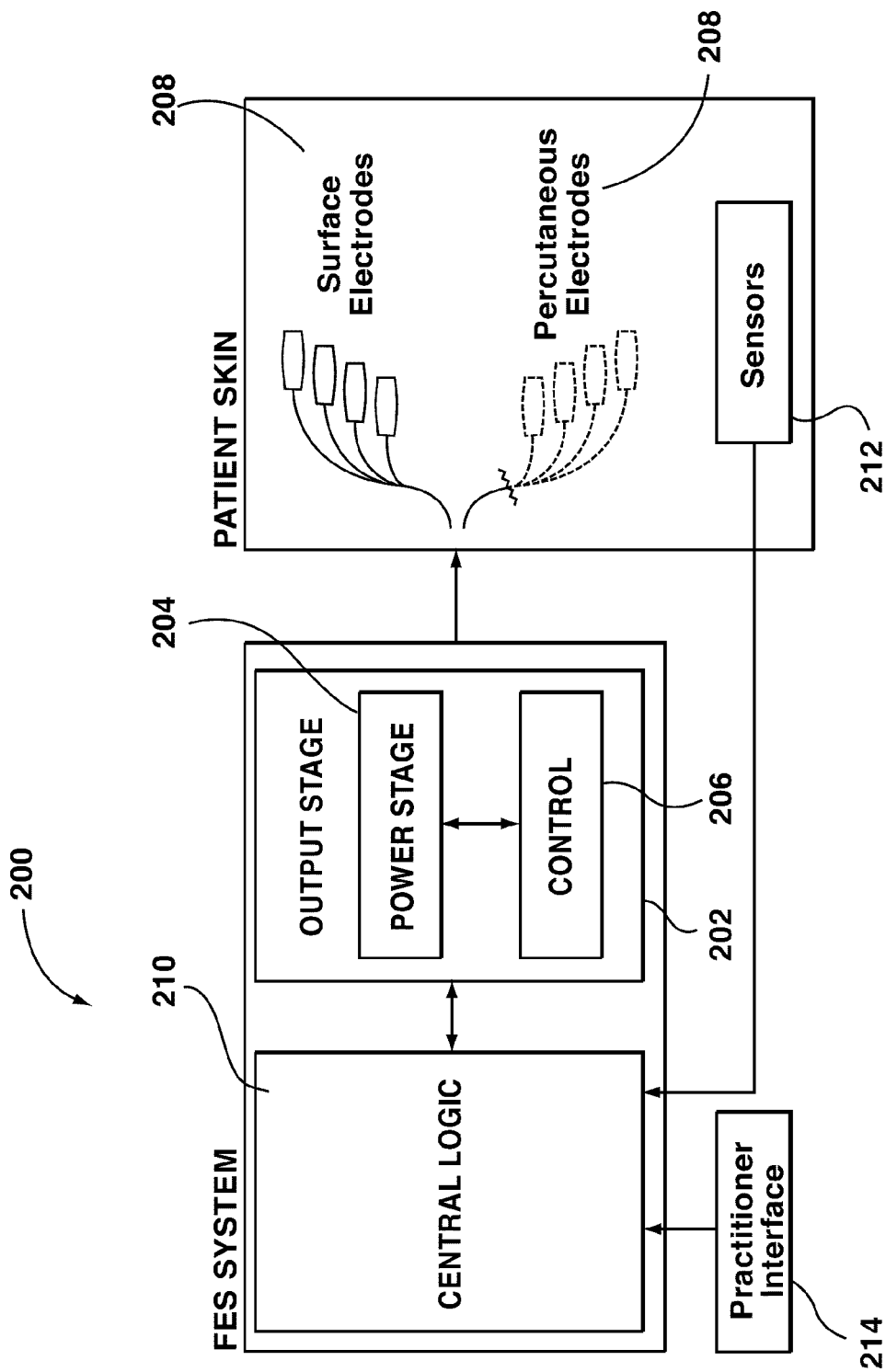
FIG. 2 is a high level diagram of a FES system, in accordance with one example embodiment.

Reference is now made to FIG. 2, which provides a high level diagram of an FES system 200, in accordance with one example embodiment. In this particular embodiment, the FES system 200 consists of an external system, however, in some example embodiments, a similar system may be designed and implemented for internal implementation (e.g. at least some of the elements as an implantable system). The system 200 generally comprises an output stage 202 comprising a power stage 204 for creating electrical pulses and a controller 206 that regulates operation of the power stage 204. The system 200 may further include, or be configured for, operative coupling with one or more stimulation electrodes 208 to deliver the pulses generated by the power stage 204 to the targeted tissues, for example, through the skin (e.g. surface/transcutaneous electrodes), directly by penetrating the body (e.g. percutaneous electrodes), the electrodes are directly implanted into the body, at least some other parts such as a portable power source (e.g. 304 in FIG. 3) is also implanted into the body, and/or at least some or all of the FES system 200 is implanted into the body, and the like. A controller, for example a central processing platform or central logic 210 is also illustratively provided to communicate intended pulse characteristics to the output stage 202, for example, external inputs from a practitioner or operator user interface 214 (e.g. via one or more activation switches, dials, footswitch(es), handswitch(es), and/or other such user operable interfaces, and/or via one or more user-selectable preprogrammed stimulation sequences stored or otherwise accessed by the system for implementation) or from another device, such as one or more physiological sensors 212 configured to regulate or influence operation of the FES system 200 based on one or more sensed physiological parameters. Example biological signals that that may be used to drive the FES system 200 can include, for example, EMG signals, brain signals, EEG, ECoG and others. Example embodiments can be applied to user interactions protocols which use such signals. For example, 4 channels of EMG may be used to assist in controlling the pulse delivery. These sensed physiological parameters may be associated with or indicative as to an effectiveness of the FES treatment in question, for example. Other control feedback sensors or detectors may also be considered by the central processing platform or central logic 210.

The structure of FES pulses for stimulation may be determined by several characteristics, for example: pulse type (current or voltage), amplitude, duration, rise time, frequency, polarity, number of phases and symmetry, which characteristics will be further described below.

Pulse type: As noted above, the provision of current regulated pulses allows the desired charge to be controlled. Inter-variable and intra-variable differences in tissue resistance that may affect such pulses may include, but are not limited to, perspiration, skin movement and increased circulation that typically result from FES, for example. In some exemplary embodiments of FES therapy, current regulation may be preferred since a desired charge is delivered to the tissue, regardless of the tissue resistance.

Pulse amplitude and duration: In general, an action potential is only generated if the membrane potential reaches a threshold membrane potential. From patient to patient, there is a range of different tissue impedances. Also, within each patient, each type of tissue may have distinct impedance. Therefore, different currents of FES generated pulses may be necessary to address these impedance variations. Also, the type of tissue being stimulated may thus become a parameter for determining the amplitude level and the pulse duration of a given FES treatment. For example, localized stimulation of small muscles generally requires shorter less intense pulses, whereas deeper muscle stimulation requires higher amplitude and longer pulse duration.

Pulse rise time: The rise time of current pulses may be relevant in providing enhanced FES treatments. For example, if the pulse rise time is too slow, the membrane potential may accommodate or adjust to the stimulus. Accordingly, despite otherwise adequate stimulation pulses, a threshold membrane potential may not be achieved and the desired neuro-muscular excitation may not occur. Similarly, an improved (i.e. decreased) pulse rise-time may translate in lower requirements for pulse amplitude to achieve a similar stimulation. Such reductions in pulse amplitude may translate in a reduction in power consumption and a reduction in the total absolute charge being applied to the tissue, which may be of particular interest in certain applications.

Pulse frequency: The frequency of pulse delivery determines the rate of action potential generation in the tissue. If the stimulation frequency is at or greater than 40 Hz, the generated action potentials create continuous muscle (tetanic) contractions. If the stimulation frequency is between 16 and 40 Hz, many individuals may feel discontinuous muscle contraction (non-tetanic contraction); however, the muscles are still able to generate a functional task. For stimulation frequencies below 16 Hz continuous, (tetanic) muscle contraction is very unlikely. The higher the stimulation frequency, the faster the muscles fatigue and the lesser the discomfort experienced by the patient. Within pulse frequencies of about 0 to 100 Hz, the stimulation frequency generally determines the rate of APs. Beyond 100 Hz, the rate of APs in not necessarily proportional to the amount of stimulation frequency. Stimulation frequencies above 1,000 Hz may incapacitate excitable tissues and thus not generate APs.

Pulse polarity and symmetry: Pulses may be monopolar (positive or negative) or bipolar (positive and negative). Bipolar pulses can be symmetric or asymmetric. The different permutations of these characteristics are illustrated, for example, in FIG. 1.

The abovementioned characteristics define the type and shape of pulses used in FES applications. For external stimulation, for example, the charge balance on the tissue is preferably maintained as excess charge build up in the tissue over time can result in galvanic processes and cause significant tissue damage and pain. For this reason, bipolar pulses that apply the same amount of charge in each direction are used most often in clinical practice. An asymmetric pulse with one negative phase at a given amplitude and duration and one second positive phase at one quarter the amplitude for 4 times the duration are believed to produce improved results for external FES applications, however, other pulse duration and amplitude ratios may also be considered in the present context without departing from the general context of the present disclosure. Depending on the application at hand, improved accuracy and control on pulse stimulation parameters may allow for a more accurate and effective treatment, not to mention improved patient safety and comfort levels. For example, the provision of reduced pulse rise times (which may effectively contribute to a reduction in pulse amplitudes (energy) utilized to generate desired muscle contractions), tight control over pulse temporal characteristics and pulse amplitude, may all contribute to a reduction in the likelihood of charge build up, and thus represent a constant opportunity for FES system improvements.

Figure 3:
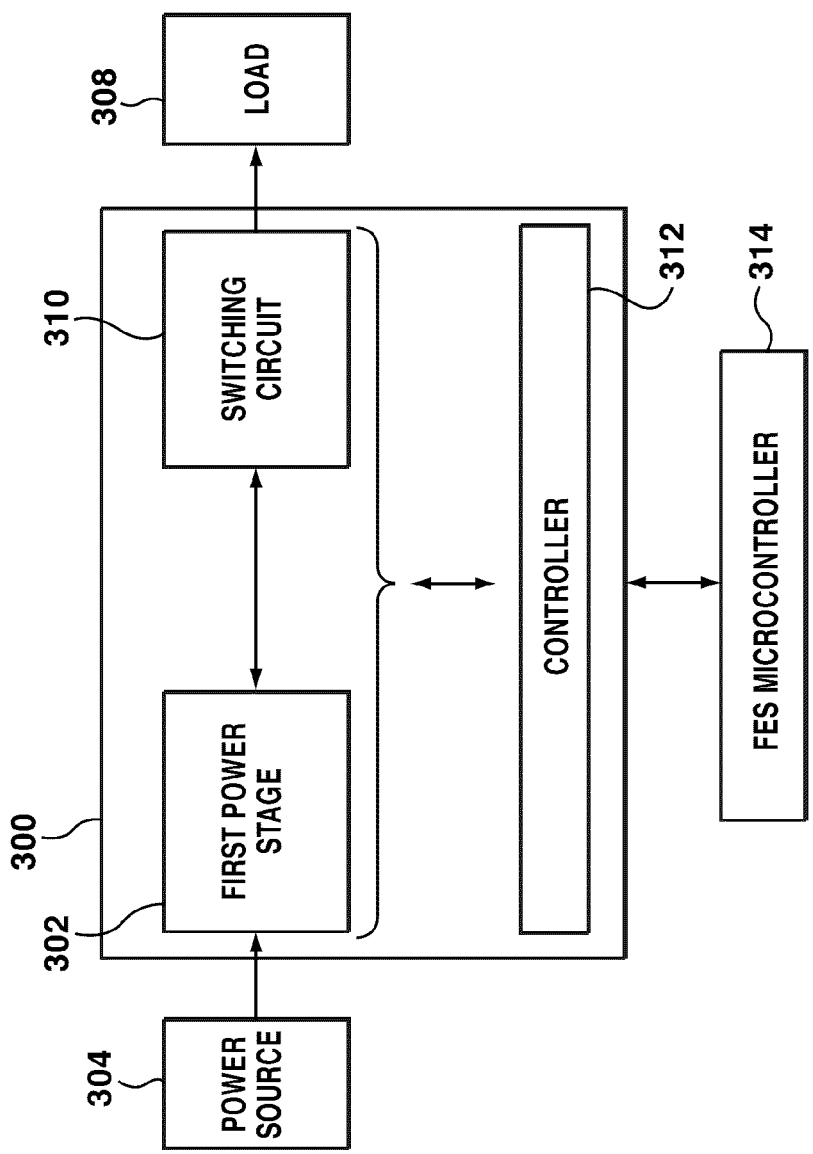
FIG. 3 is a schematic diagram of an output stage of a FES system, in accordance with one example embodiment.

With reference to FIG. 3, and in accordance with one example embodiment, an exemplary output stage 300 is generally depicted. In this example, the output stage 300 generally comprises a first power stage 302 operatively coupled to a power source 304, such as a battery or the like, to increase the voltage supply available to implement various FES pulse sequences/parameters to a load 308 via a switching circuit 310. A controller 312 is also provided to control various operational aspects of the output stage 300, such as voltage and/or current regulation and control to regulate FES parameter values and/or implement various safety procedures, as well as control operation of the pulse generating circuit in accordance with one or more selectable FES treatment sequences/parameters. A general FES microcontroller 314 may also be provided in providing overall control features, for example in the context of an overall FES system incorporating output stage 300. In one embodiment, the first power stage 302 includes a digitally controlled switch-mode power supply (SMPS). In order to achieve the desired pulse response time while changing the direction of the current, (e.g. from V to ¼V in a short time frame), in one example embodiment, the first power stage 302 can include, for example, four SMPS power supplies in series, so that switching or relaying in of all of the power supplies can result in a total voltage V, and switching or relaying in only one of the power supplies can allow the voltage supply to readily drop to ¼V.

The switching circuit 310 will now be described in greater detail. To produce bipolar asymmetric pulses, for example, stimulation must generally be switched from a positive/negative current at a given amplitude, followed by a current of the opposite polarity at a fraction of this amplitude (e.g. from I to −¼I in one example). The switching circuit 310 can be used to change the voltage and current direction of the load quickly, such as by way of switches in an H-bridge configuration. Accordingly, the output stage 300 can quickly change the amplitude of the voltage V to ¼V as well as the direction of the current flow to the load.

Figure 4:
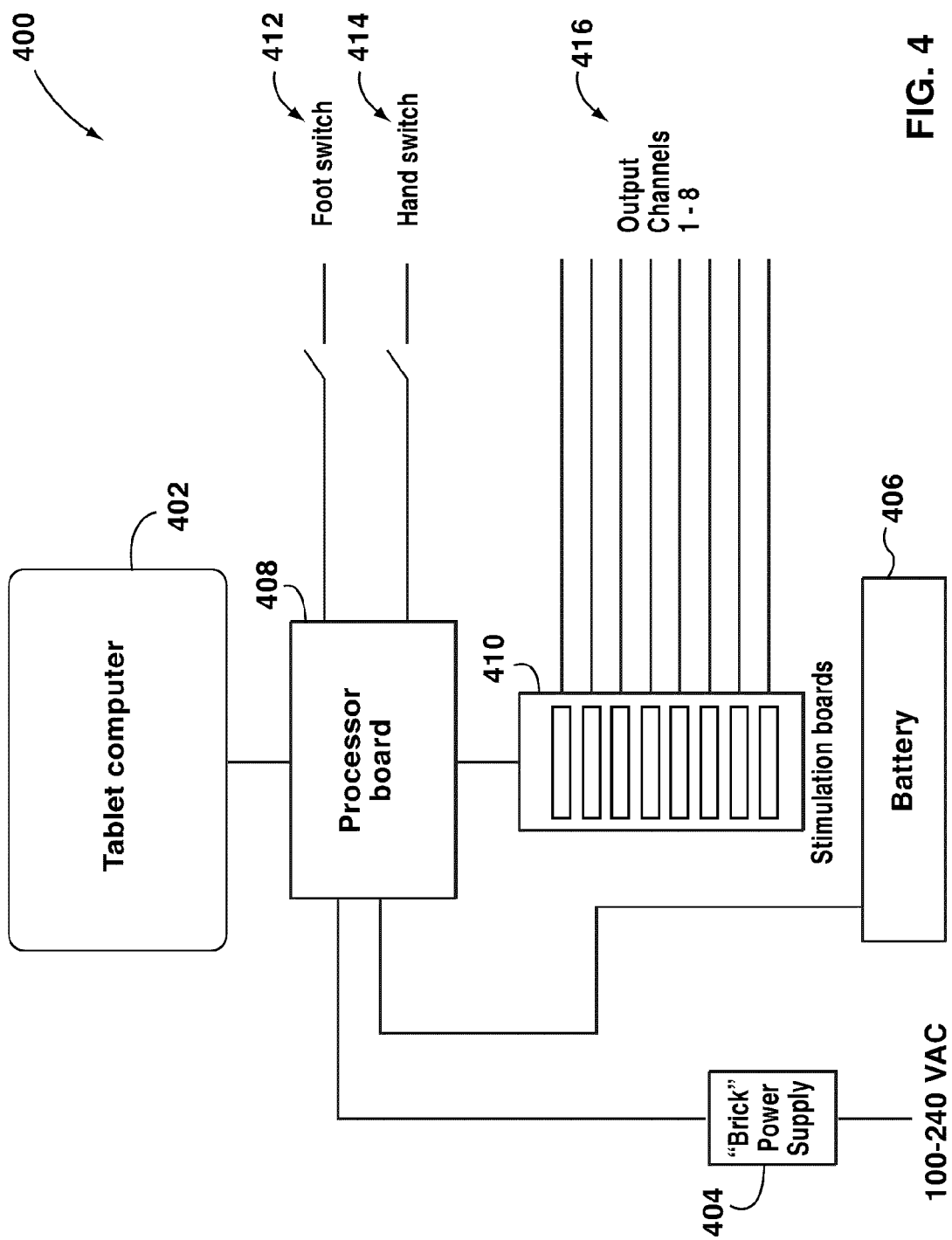
FIG. 4 is a high level diagram of a FES system, in accordance with another example embodiment.
Figure 5:
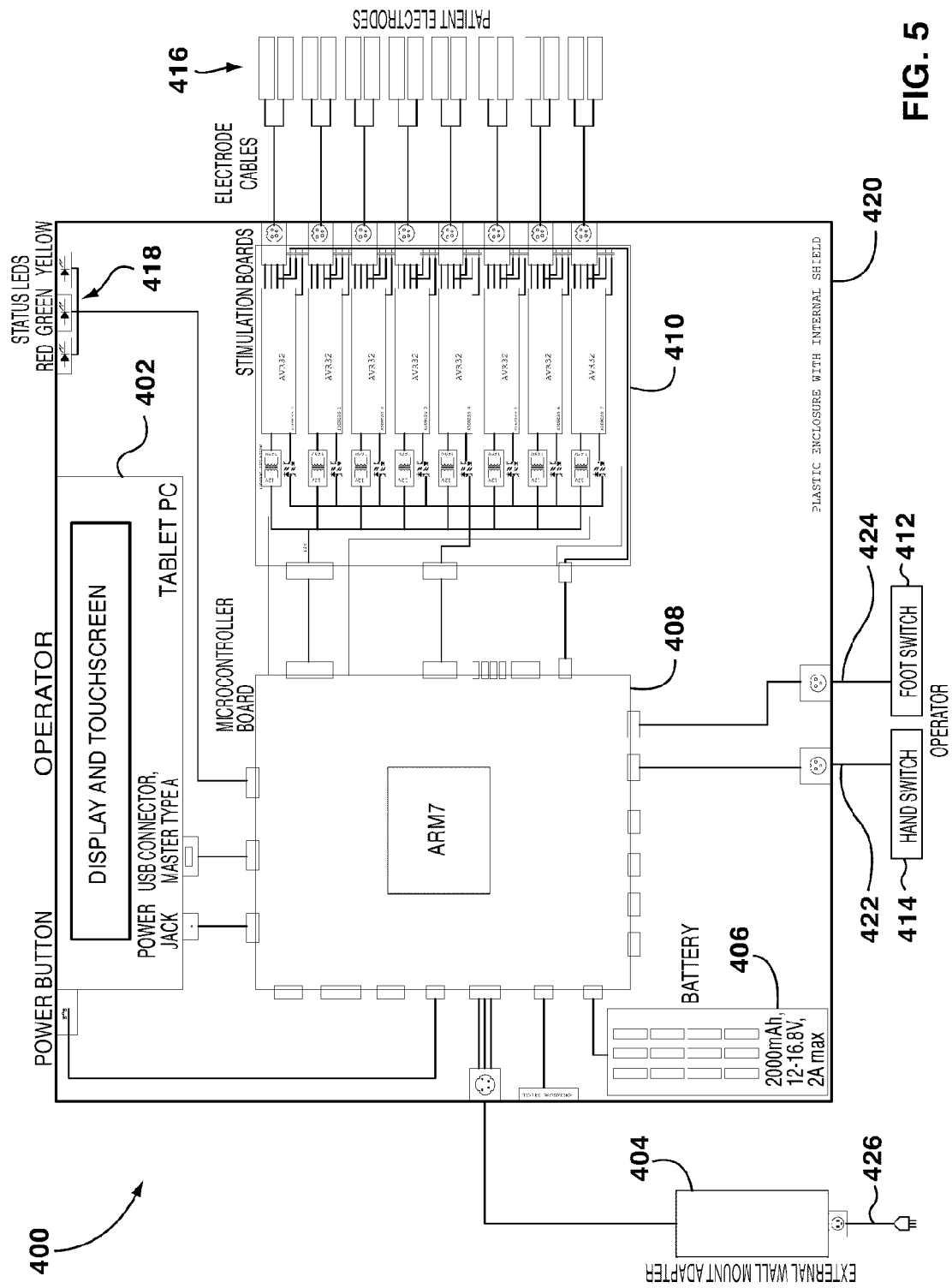
FIG. 5 is a schematic diagram of the FES system of FIG. 4, in accordance with an example embodiment.
Figure 6A:
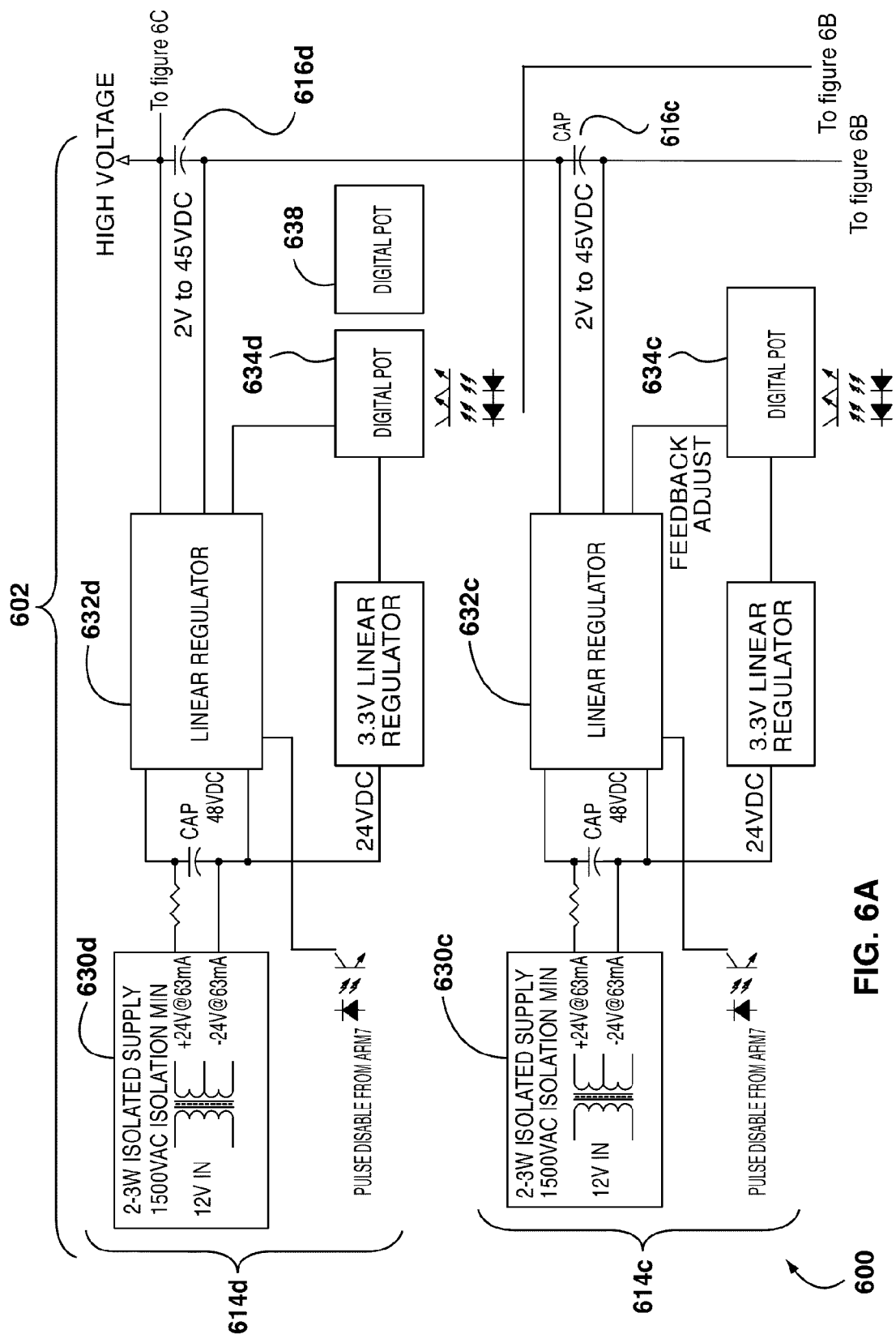
FIGS. 6A, 6B, 6C and 6D (hereinafter each or collectively referred to as "FIG. 6") illustrate a detailed schematic diagram of one output stage of a FES system, in accordance with an example embodiment.
Figure 6B:
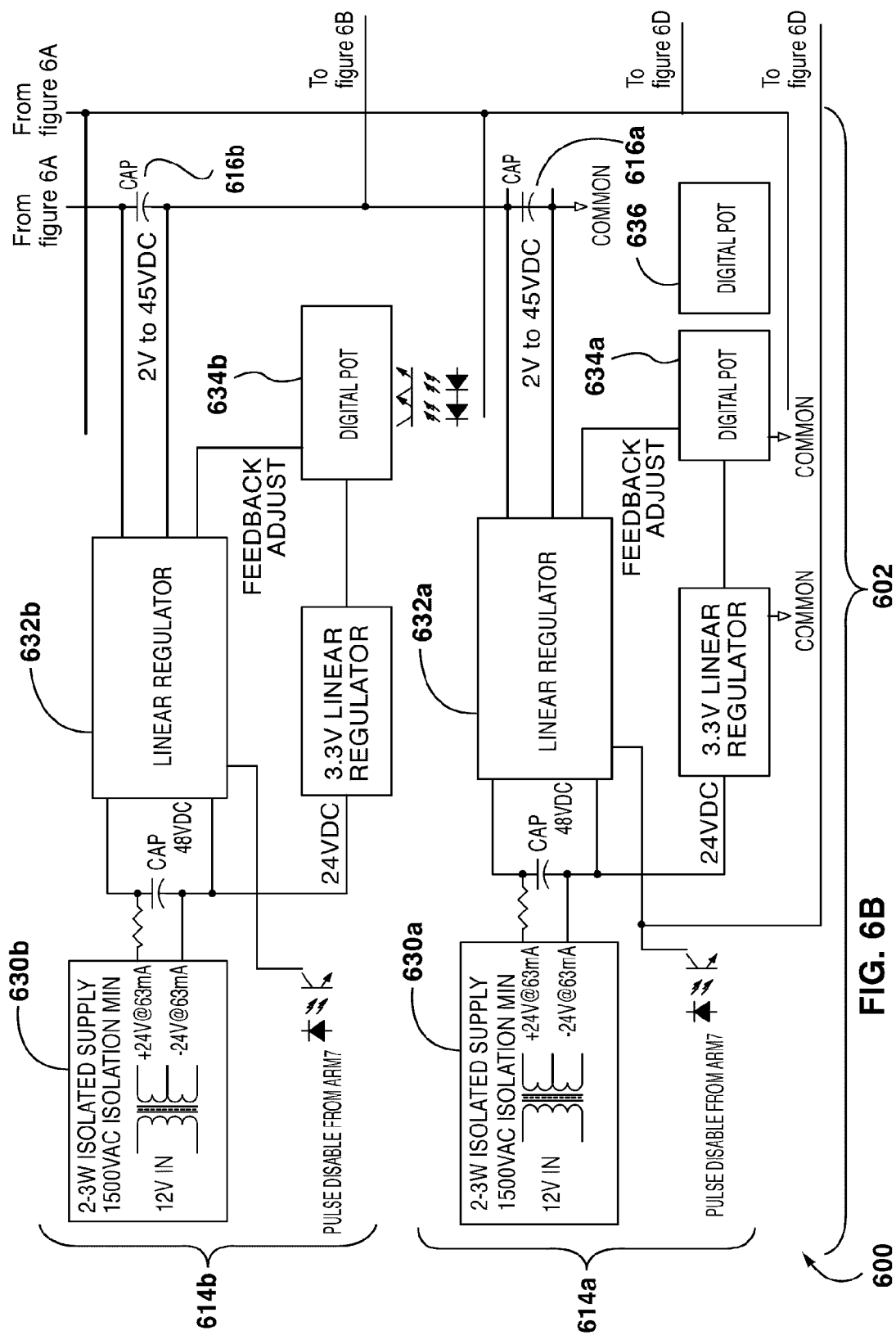
Figure 6C:
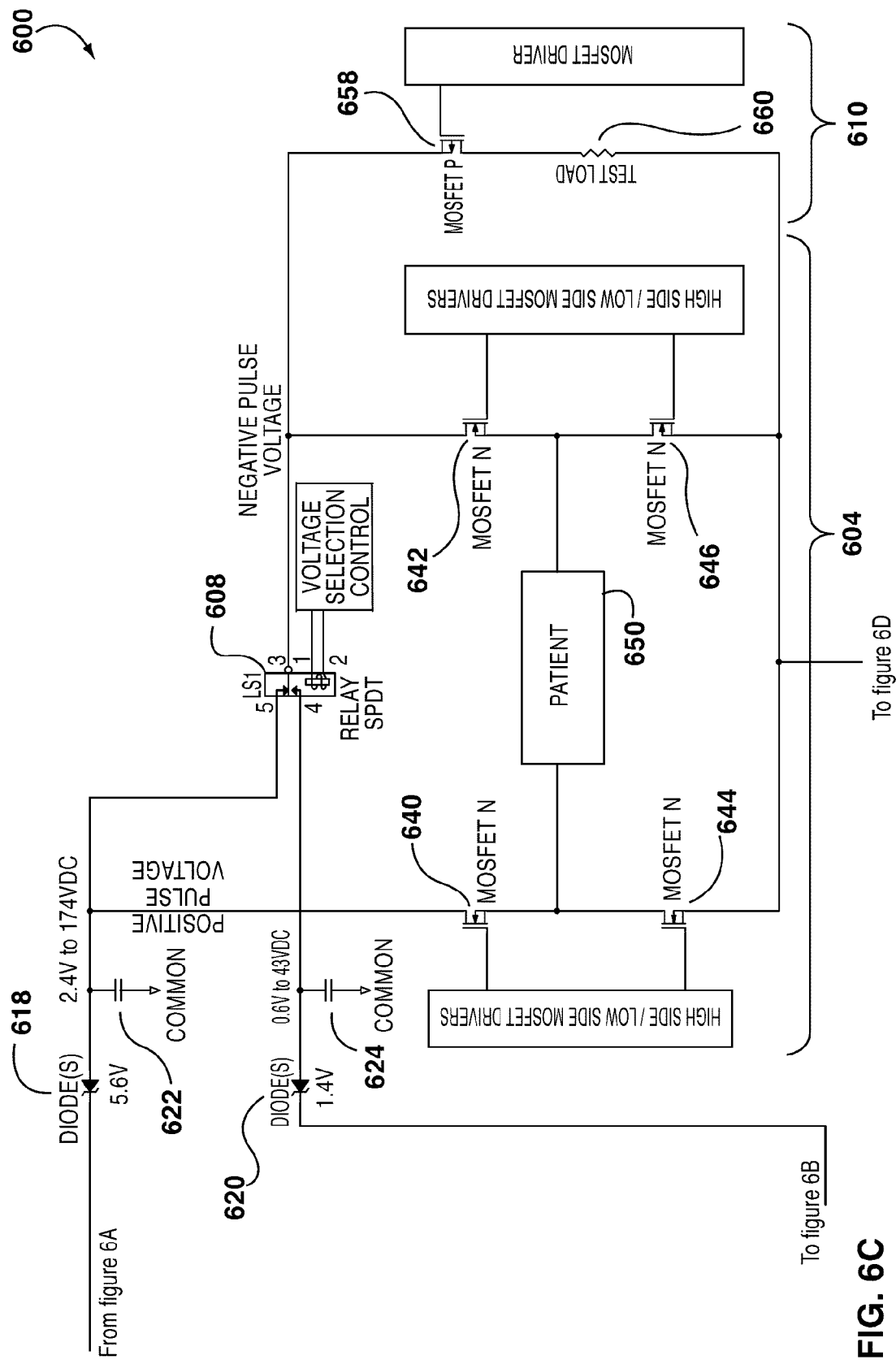
Figure 6D:
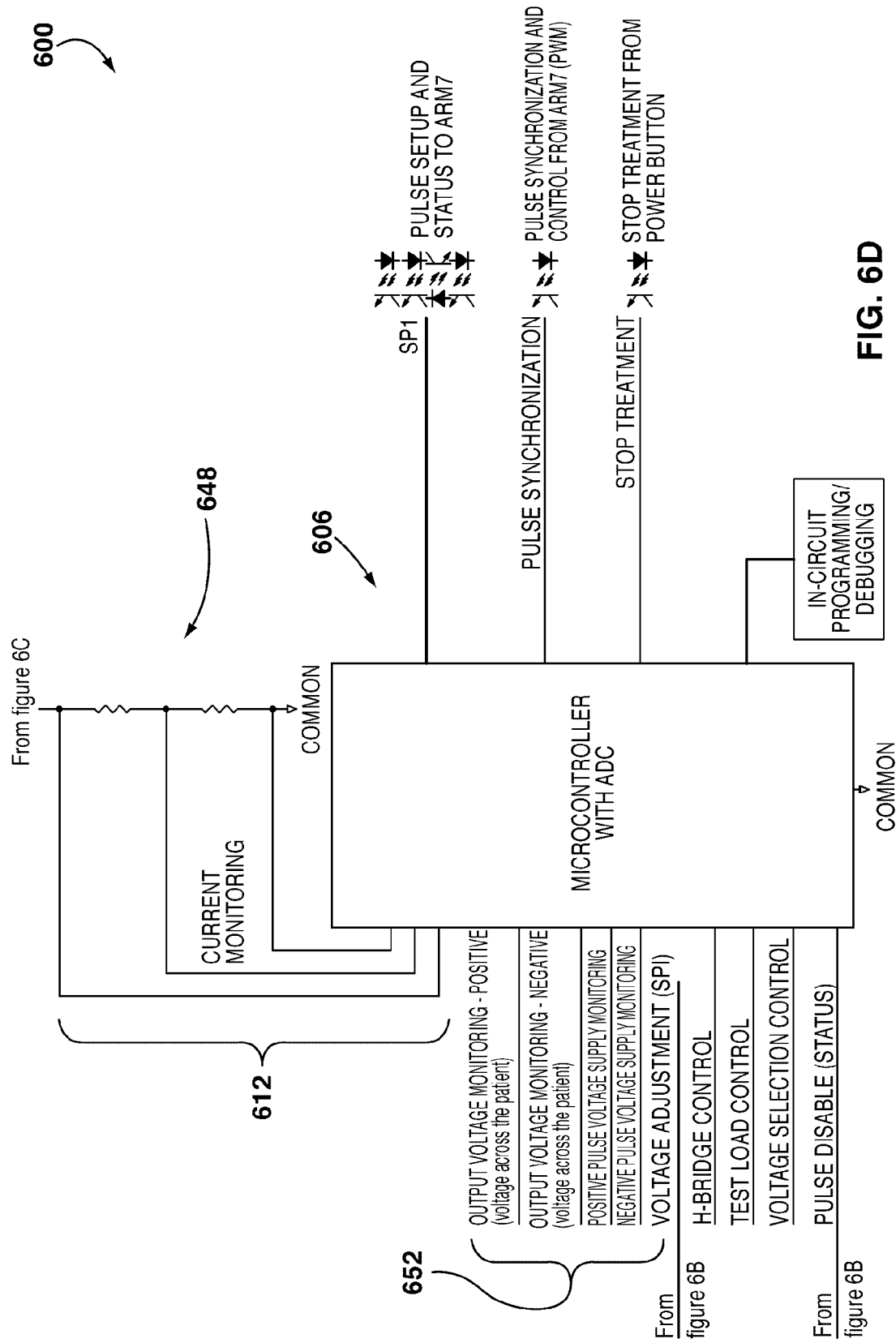

FIG. 4 is a high level diagram of another example FES system 400, in accordance with an example embodiment. FIG. 5 is a detailed schematic diagram of the FES system 400. The FES system 400 may include a tablet computer 402, a power supply 404, a battery 406, a processor board 408, one or more stimulation boards 410 (eight stimulation boards shown), and a plurality of output channels 416 (eight output channels shown).

In an example embodiment, the battery 406 is selected for 12V to 16.8V, 2000 mAH with a 2 A max charge/discharge current. This lower power rating was found to provide greater stability and less prone to disruptions. In an example embodiment, each generated constant voltage pulse can include a faster rise time resulting in a lower required specified target steady state current than when compared to a rectangular constant current pulse (due to the capacitance of the patient or other elements) or a constant voltage pulse having a slower rise time requiring a higher required specified target steady state current. The system can, for example, can save the amount of power consumed or total energy required to be provided by the power source (e.g. less current required per pulse as well as overall lifetime of the battery 406 than compared to other systems have a higher current draw).

A computer device such as the tablet computer 402 includes at least a memory, a device controller, a display screen, a communications subsystem (e.g. wireless and/or Ethernet) to communicate over a local area network and/or the Internet, and a user input device such as a touchscreen. The tablet computer 402 facilitates operator ease of use. Displayed on the tablet computer 402 is a user interface. The tablet computer 402 can connect to the Internet for transfer of prescriptions and patient data, described in greater detail herein. The tablet computer 402 is also used to control the processor board 408 and effectively the stimulation boards 410. The controls are typically isolated so as not to damage the tablet computer 402 and to isolate the patient from earth ground and line voltage. Example controls on the user interface can provide the user with an option to specify a treatment protocol for the particular patient, such as the target steady state current value, the pulse width, the pulse frequency, and any changes of these parameters over time. Through the user interface, in some example embodiments, the user can pre-plan these and other parameters as a procedure by storing the plan in memory (or other remotely accessible storage devices), for implementation by the processor board 408.

The processor board 408 runs a real-time operating system in order to control the delivery of the stimulation pulses, in accordance with some example embodiments. The processor board 408 may include an ARM7 microprocessor, for example. This connects to the eight stimulation boards 410, which are individually operably connected to eight output channels 416, for example. The processor board 408 can also be activated using manual switches such as footswitch 412 and/or handswitch 414. Other inputs such as external sensors or control feedback sensors (not shown here) may also be coupled to the processor board 408 or stimulation boards 410. In some example embodiments, these switches 412, 414 may be dead-man switches, meaning the user must hold down the switch to start the treatment, and releasing the switch automatically stops the treatment.

The communication protocol provides a method for transferring new treatment programs from the tablet computer 402 to the processor board 408. Once the program is loaded, it is stored in the non-volatile eeprom memory, for example. The treatment program defines the pulse characteristics (such as frequency, amplitude, pulse duration, pulse type, and pulse train profile(s)). The program also specifies the duration of the treatment and how it is triggered (for example through analog or digital user input). The commands allow the tablet computer 402 to instruct the processor board 408 to start a treatment, pause a treatment, resume treatment, stop a treatment. The status information from the processor board 408 includes data from the isolated digital/analog patient inputs (envelope information only) and alarm information.

The user interface application of the tablet computer 402 can be configured to handle the following tasks:

1. Treatment selection. This involves selection appropriate treatment for the patient. It also may involve creating/editing existing treatments or loading new treatments through a service USB or download treatments from the Internet.

2. Sending configuration file to the stimulator. It is assumed that a new file is sent to the microcontroller board each time a treatment starts. The treatment file is a script of actions that the stimulator boards carry out. The tablet computer 402 translates the script into a compressed binary script. The basic functions of the script file are as follows:

Start condition: defines input state and perhaps phase of the treatment FES to execute the procedure. For example waiting for a button press.

Synchronization to other channels. Waiting for other channels to complete their control loops.

Running parameters: defines frequency, pulse type and amplitude, allowed current range for the output (two sets of thresholds: warning and error levels).

Loops for repeating sequences.

Terminating conditions (such as time out, change in input state).

3. Reading and displaying serial number, firmware version of the microcontroller. The tablet computer 402 reads status information such as error flags, battery level, currently applied pulse type, pulse frequency, pulse duration, target output current, and actual average positive and negative current levels for each of the outputs.

4. Reading and displaying the status of the 4 ADC input values.

5. Start/stop treatment. Pressing a button on the touch screen starts and stops the treatment. The unit contains a power button that is used to stop the treatment in the event that the tablet computer 402 becomes unresponsive. In some example embodiments, starts and stops on the user interface can be implemented as dead man switches, meaning the user must hold down the button to start the treatment, and releasing the button automatically stops the treatment.

6. The tablet computer 402 manages its own power to minimize the power consumption.

Referring to FIG. 5, an enclosure 420 can house the components of the system 400. The enclosure 420 and connector cables may include plastic or other non-conductive material. The enclosure 420 can have an internal shield. At least some of the connector cables including cables 422, 424, 426 can be treated with ferrites or other suitable materials in order to block or reduce electromagnetic interference.

Referring to FIG. 5, status LEDS 418 can include red, green and yellow status LEDs which are mounted in the enclosure and connected to the processor board 408. The status LEDs 418 are used, in some example embodiments, to indicate AC power status (green LED on or off), treatment running (yellow LED flashing), and error (red LED on).

FIG. 6 is a detailed schematic diagram of one output stage 600 of a FES system, such as the FES system 400 (FIG. 4), in accordance with an example embodiment. The output stage 600 includes a controllable constant voltage pulse generator. For example, each of the eight output channels 416 (FIG. 4) may be driven by a respective output stage 600, to apply a signal to an area of the patient 650. In some example embodiments, all channels 416 can have the same frequency, and the leading edges of the pulses can be synchronized (e.g. to within 10 us). In other example embodiments, at least some or all of the channels 416 may have different frequencies. In some example embodiments, at least some or all of the channels 416 may have different phases (e.g. phase shifted or with different leading edges).

Referring still to FIG. 6, the output stage 600 may include a substantially constant voltage supply 602 having a controllable output voltage, a switching circuit 604, a controller 606 (e.g. microprocessor 606), a relay 608, an alternate path 610, and a signal detector 612. The substantially constant voltage supply 602 can include four power supplies 614a, 614b, 614c, 614d (each or individually referred to as 614) in series, which can each be 45 V, for example. In some example embodiments, these four power supplies may be used because these parts are easier to supply and less expensive than one large power supply. Further, this allows the voltage to be readily divided to provide asymmetric pulses. For example, one power supply 614a can be tapped for applying a negative voltage which is one quarter of the positive voltage. In other example embodiments, more or less power supplies 614 can be used, such as one or two.

The power supplies 614 each charge a respective large capacitor 616a, 616b, 616c, 616d (each or individually referred to as 616). This allows the capacitor 616 to discharge to provide the large current spike at the start of the pulse. In another embodiment, the substantially constant voltage supply 602 can include a power supply that was able to deliver suitable amounts of current, which may not need the capacitors 616. However, using capacitors in this manner allows using of smaller power supplies 614, saving cost, heat generated, and space. Additional large capacitors 622, 624 can be used to store charge to provide the required amounts of current. The large capacitors 622, 624 therefore provide charge to allow fast pulse rise times which are predominantly defined by the switching speed time of the switches in the switching circuit 604. The particular power supplies 614 that are used can be adjusted to provide 2 to 45 volts each, for a total of 8 to 180 volts, for example.

Each power supply 614 may each include an isolated DC-DC module 630a, 630b, 630c, 630d (each or individually 630). Each of the outputs from these are regulated by a respective linear regulator 632a, 632b, 632c, 632d (each or individually 632). The voltage of each regulator 632 is set by a respective digital potentiometer 634a, 634b, 634c, 634d, which can be for example a maximum of 100 k ohms. The output of each regulator 632 is connected in series creating a variable output supply with a range of 8V to 192V. The effective range of the supply is adjusted to 2.5V to 160V. The achievement of the specific minimum value 2.5V is explained in greater detail herein with respect to the Zener diode 618.

The microcontroller 606 uses a Serial Peripheral Interface (SPI) port to send data to the digital potentiometer 634 to set the voltage of each of the 4 linear regulators 632. The data to each potentiometer 634 can be sent independently to each other. The first regulator 632a (connected to the common) can use an additional digital potentiometer, such as 100 k ohm potentiometer 636, to achieve greater resolution. The high regulator 632d (connected to high voltage output) can use an additional 20 k ohm potentiometer 638, to achieve greater resolution (at 45V output the individual regulator has a maximum step size of 0.2V). Regulators 632b and 632c can use only the single 100 k digital potentiometer 634b, 634c, for example.

The most power intensive pulse type is expected to deliver 4 W. Each of the power supplies 614 can be used to charge the large capacitor 616 (e.g. 470 uF or larger). The maximum ripple during normal operation is expected to be <24 VDC (based on two 16 ms, 125 mA pulses). During normal operation, the maximum current from the DC-DC supply is limited to 60 mA (using a 100 Ohm resistor with maximum ripple 6 VDC on each module).

In order to provide a minimum voltage of about 2.4 volts, a Zener diode 618 is provided at the output of the voltage supply 602 to the switching circuit 604. The output voltage is dropped by 5.6V as a result of the Zener diode 618. A 1.4V voltage drop applies for the ¼ negative supply as a result of Zener diode 620, providing a minimum of 0.6V. The upper range is limited by regulation error and supply ripple. The required voltage level settings of the power supplies 614 can take into account the voltage drop from the Zener diodes 618, 620 to the patient 650.

The switching circuit 604 can include an "H bridge" configuration composed of several metal-oxide-semiconductor field-effect transistor (MOSFET) switches, for example four n-channel MOSFET switches 640, 642, 644, 646. This circuit configuration allows the current to flow though the patient 650 in either a positive or negative direction, using switching control of the switches 640, 642, 644, 646. For example, a positive pulse can be activation of switches 640, 646, while a negative pulse can be activation of switches 642, 644. The rise time of the voltage pulse is primarily determined by the switching speed of the MOSFET switches 640, 642, 644, 646. The relay 608 can be used to select all of the power supplies 614a, 614b, 614c, 614d to apply a relatively high specified voltage level. The relay 608 can be used to activate one of the power supplies 614a to readily apply one-quarter of the voltage level (e.g. for asymmetric bipolar pulses).

The MOSFET switches 640, 642, 644, 646 are operated by high-side/low-side drivers with bootstrap capacitors. Between pulses the low-side MOSFET switches 644, 646 can be activated, shorting patient electrodes together. The MOSFET signals are operated by the microcontroller 606.

The H-bridge circuit is used to control patient pulses, such the start and stop of each pulse using the signals from the voltage supply 602. For symmetric pulses, positive and negative pulses are powered by the four power supplies 614 in series. For asymmetric pulses, the positive pulse is powered by the four power supplies 614 in series. However, the negative pulse of the asymmetric pulse can be powered by a single power supply 614a, which generates ¼ of the voltage from the high voltage supply. The voltage selection between symmetric and asymmetric pulses is done with the latching relay 608.

Referring to signal detector 612, this can be used for current measurement, for example the steady state current that is being applied to the patient 650. Typically, this current value is measured near the end of the pulse. The current generated from the H-bridge circuit 604 is measured using shunt resistor 648. It was found that increased resistance of the shunt resistor 648, greater than 10 Ohms, provided more favourable and consistent measurements. The current reading is connected directly to the pins of the microcontroller 606 and measured using the internal analog-digital converter (ADC). The measured value is processed by the microcontroller 606 to calculate resistance between electrodes. The processor measures the current (steady state) for the positive pulse, for the negative pulse (steady state), current through the test load, and the off current. The readings (envelope) are stored as status to be sent back to the processor board 408 (FIG. 5).

Referring to another signal detector 652, this can be used for voltage monitoring. The microcontroller 606 reads the supply voltage connected to the positive pulse output voltage across the patient and the negative pulse output voltage across the patient. The processor measures the voltage of the positive pulse supply, negative pulse supply, and digital supply. The readings (envelope) are stored as status to be sent back to the processor board 408 (FIG. 5). Note that the signal detectors 612, 652 may be readily used to calculate the present patient capacitance, if desired.

In some example embodiments, the information detected by the detectors 612, 652 can be stored in a local memory, and/or sent to a remote server. In some example embodiments, the system can be used for monitoring the patient's skin resistance, and the skin resistance "profile" can be used to determine if a wrong person is being delivered the therapy instead of the person for whom the therapy was originally prescribed. This may include the native impedance parameters, and/or any responses to FES treatment parameters. The patient profile can be used as a signature for that patient. This can be used, for example, to prevent fraud and to monitor what the stimulator has been used for during previous treatments.

Referring to the alternate path 610, the output circuit contains a p-channel MOSFET switch 658 and a 500 ohm test load 660. The load 660 can be activated independent of the H-bridge 604. The test load 660 is used to test the current measurement and power supply circuits before the treatment. The test load 660 is also used to discharge high voltage supply (the output capacitance of the power supply is approx 3.3 uF) if output voltage for the next pulse needs to be lower than the current pulse.

Generally, as described above, the stimulation pulse is a constant voltage pulse. However, the stimulation dose is specified in terms of target steady state current, for example as received or specified by the practitioner via the tablet computer 402 and processor board 408 (FIG. 5). The steady state current is the current through the electrodes at the end of a positive pulse (after an exponential decay). To achieve this, the microprocessor 606 measures the current actually delivered, calculates the steady state resistance of the patient 650, and adjusts the voltage to deliver the desired current. This is done by passing the current through the shunt resistor 648 in series, and then measuring that voltage with an analog to digital converter. The microprocessor 606 does the calculation and sends out the control signals to adjust the voltage. The initial calibration is first performed using a few sub-threshold pulses (that do not actually stimulate the patient and cannot be felt). After the real stimulation starts, the measurement is repeated during every pulse to ensure that the resistance is not changing. Constant voltage pulses are suitable for this application since the patient resistance typically does not materially change within any given pulsewidth.

Each stimulation channel is capable of generating asymmetrical/symmetrical biphasic waveforms with following characteristics:

Target current range 0 to 125 mA. Adjustment in 0.05 mA steps for current setting below 5 mA, 0.1 mA steps for current setting between 5 mA and 15 mA, 0.5 mA steps for current setting above 15 mA. Steady state target output current error +/−0.5 mA for currents up to 15 mA. Steady state target output current error +/−1 mA for currents above 15 mA. The maximum current may be limited by the skin resistance and the maximum output voltage of the circuit. The minimum current may be limited by the skin resistance and the minimum output voltage of the circuit.

The actual amplitude levels may be limited by software depending on frequency. With a load resistance of 500 ohms, the steady state output current can be set to not exceed 80 mA at DC, 50 mA between DC and 400 Hz, 80 mA between 400 and 1,500 Hz, and 100 mA above 1,500 Hz.

When operating the stimulator with actual patient there will be an inrush current at the start of the pulse. The pulse width range can be from 0 to 16,000 us (adjustment in 10 us range, output error 10 us). Pulse width may be limited by the frequency setting. Minimum time between pulses is 200 us. The pulse frequency can be from 1 to 2,000 Hz (adjustment in 1 Hz step, output error 1 Hz).

The maximum average output power can be limited to 4 W for each channel (the most power intensive asymmetric pulse is 125 mA (800 us) positive pulse, 31 mA (3.2 ms) negative pulse, frequency of 100 Hz). The most power intensive symmetric pulse is 125 mA (800 us) positive pulse, 125 mA (800 us) negative pulse, frequency of 100 Hz.

The maximum voltage generated by the output stage for the asymmetrical pulses can be 160 VDC for positive pulse and 40 VDC for negative pulse.

The maximum voltage generated by the output stage for the symmetrical pulses can be 160 VDC for positive pulse and 160 VDC for negative pulse.

The minimum voltage generated by the output stage for the asymmetrical pulses can be 2.5 VDC for positive pulse and 0.6 VDC for negative pulse.

The minimum voltage generated by the output stage for the symmetrical pulses can be 2.5 VDC for positive pulse and 2.5 VDC for negative pulse.

The rise time of the pulse is under 2 ns (rise time measured from 10% value to 90% value) measured at the output of the stimulator with standard skin model load. Slightly longer rise times (<50 ns) may be used to minimize electromagnetic emissions.

The maximum voltage across patient leads can be 500 VDC.

The target skin resistance is in the range of 500 Ohm to 10 kOhm. At higher skin resistance values, the output current will be limited by the skin resistance. 125 mA is supported on skin resistance up to 1,280 Ohm. 50 mA is supported on skin resistance up to 3,200 Ohm. At 10 kOhm the maximum current that can be supplied is 16 mA. Minimum current for 500 Ohm is 5 mA (2.5V minimum output). Adjustment step size increases with the output voltage. At the highest voltage the step size is 0.2V which produces the maximum 0.4 mA current step size at 500 Ohm load.

Low voltage short series "calibration pulses" (with amplitude below 10V) are applied before the start of the treatment to measure the resistance of the electrode/skin. If the pulse duration, as dictated by the protocol, is less than 100 microseconds, then the voltage for these pulses is delivered based on "calibration pulses" only. If the pulse duration is greater than 100 microseconds, the skin resistance is re-measured after each pulse and the voltage is adjusted.

Sample current, skin resistance and step size are as follows:

For 0-5 mA, 500 Ohm: output voltage range: 0-2.5V with 0.05 mA step size this requires 0.025V step size (the minimum output of the circuit is 2.5V). For 0-5 mA, 2,000 Ohm: output voltage range: 0-10V with 0.05 mA step size this requires 0.1V step size (the minimum output of the circuit is 2.5V). For 0-5 mA, 10,000 Ohm: output voltage range: 0-50V with 0.05 mA step size this requires 0.5V step size (the minimum output of the circuit is 2.5V).

For 5-15 mA, 500 Ohm: output voltage range: 2.5-7.5V with 0.1 mA step size this requires 0.05V step size. For 5-15 mA, 2,000 Ohm: output voltage range: 10-30V with 0.1 mA step size this requires 0.2V step size. For 5-15 mA, 10,000 Ohm: output voltage range: 50-150V with 0.1 mA step size this requires 1V step size.

For 15-125 mA, 500 Ohm: output voltage range: 7.5-62.5V with 0.5 mA step size this requires 0.25V step size. For 15-125 mA, 2,000 Ohm: output voltage range: 30-150V with 0.5 mA step size this requires 1V step size. For 15-125 mA, 10,000 Ohm: output voltage range: 150-160V with 0.5 mA step size this requires 5V step size (maximum current is limited due to voltage limitation).

In some example embodiments, the system 600 of FIG. 6 can therefore be used to apply the signal pulses to the patient which are illustrated in any one of FIGS. 9 to 12.

Figure 13:
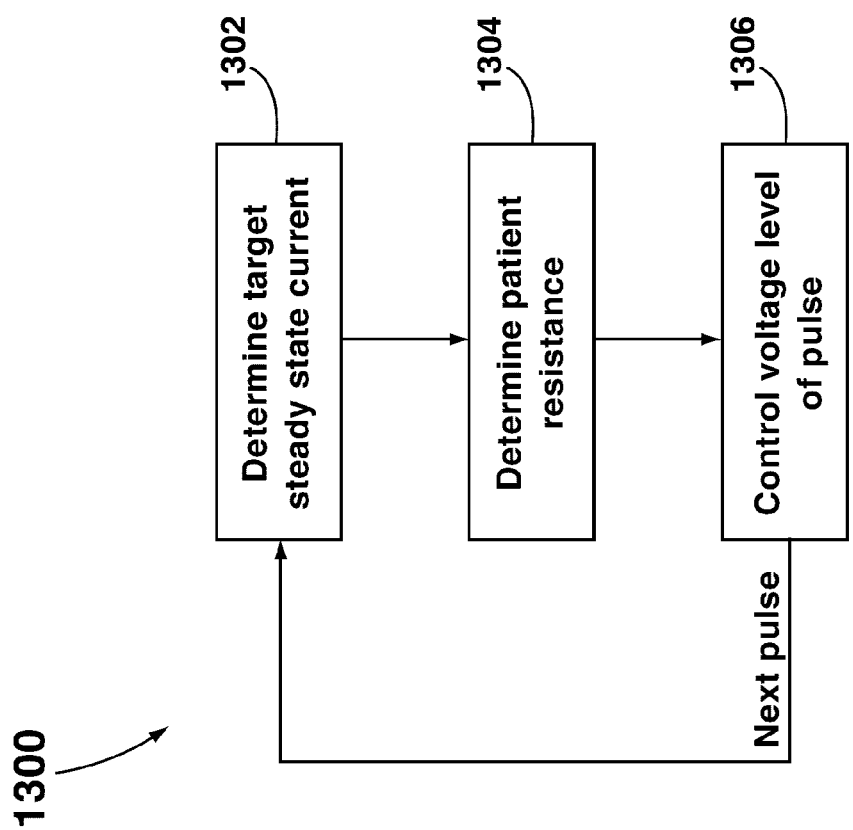
FIG. 13 illustrates a flow diagram of an exemplary method for applying signal pulses to the patient, in accordance with an example embodiment.

FIG. 13 is a flow diagram of a method 1300 for applying signal pulses to a patient, in accordance with one example embodiment. The method can be implemented by a controller or microcontroller, for example. The flow diagram 1300 can also represent functional modules or blocks, which can be state-based. The method 1300 is for controlling a functional electrical stimulation system for providing pulse stimulation to an area of a living body by way of one or more electrode leads applied to the area, the area including an associated resistance element and an associated capacitance element, wherein the electrical stimulation system includes a pulse generating circuit having a controllable output voltage to generate constant voltage pulses to the one or more electrodes, wherein the corresponding current signal of each constant voltage pulse includes a spike followed by an exponential decay to a steady state current value.

At event 1302, the method 1300 includes determining specified target parameters, including at least a specified target steady state current value to be applied to the area. At event 1304, the method includes determining the present resistance of the patient. At event 1306, the method includes controlling the pulse generating circuit to generate a constant voltage pulse to the one or more electrode leads at a calculated voltage level which achieves the specified steady state current value to the area.

Referring to event 1302, the specified target steady state current value can be input by a practitioner or user, for example through a user interface of a tablet computer, or by accessing the specified target steady state current value from a pre-programmed dosage schedule stored in a memory or remote server.

Referring to event 1304, a signal detector can be used for detecting signal parameters associated with the area of the living body, such the actual steady state current that is being applied. The applied voltage to the patient is also known or can be detected using a voltage detector. This can be used to calculate the present resistance of the patient. In some example embodiments, the present resistance can be estimated for each pulse, or periodically (e.g. one pulse in every specified number of pulses or time duration), or can be calculated as an average resistance (or moving average) over a specified number of pulses or a period of time. The resistance of the patient can be initially estimated by applying one or more sub-threshold pulses (e.g. non AP stimulating) to the area from the pulse generating circuit, prior to the start of the actual procedure.

Referring to event 1306, the calculated voltage level is calculated from the associated resistance element of the patient and the specified target steady state current value using Ohms' Law (e.g. V=R*I). Note that, in some example embodiments, the calculated voltage level is calculated without consideration of a value of the associated capacitance element.

The method 1300 can be configured in a loop, as shown. For example, in the next iteration, referring again to event 1302, the method 1300 may include determining the next specified target steady state current value to be applied to the area (this step can be skipped if the value is the same). At event 1304, the method 1300 includes determining the present patient resistance (e.g. based on the presently detected patient readings of the previous pulse). At event 1306, the method 1300 includes controlling the pulse generating circuit to generate the next constant voltage pulse to the one or more electrode leads at the next calculated voltage level which achieves the next specified steady state current value to the area.

The constant voltage pulses may provide sequential bipolar pulse stimulation, which includes a pulse sequence including a positive constant voltage pulse and a negative constant voltage pulse.

Figure 14:
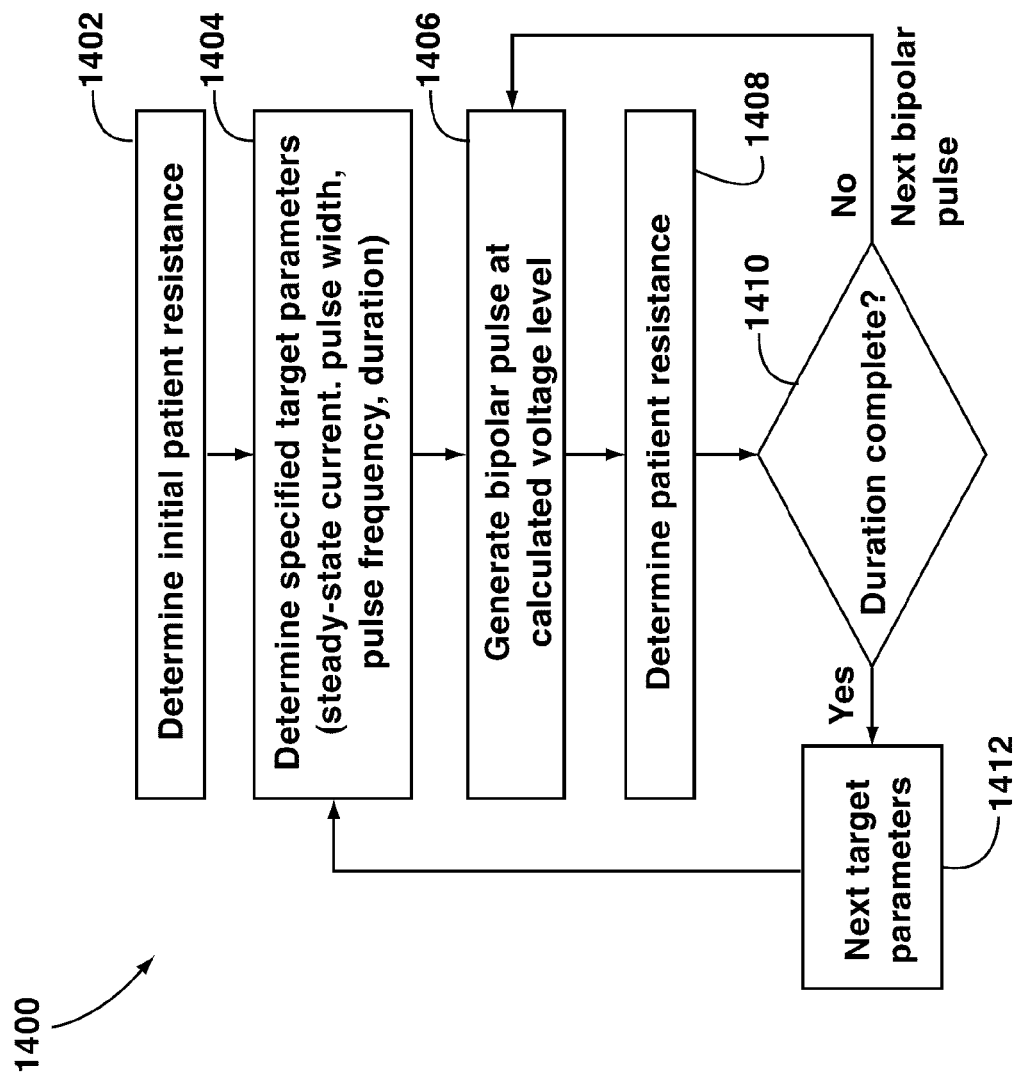
FIG. 14 illustrates a flow diagram of another exemplary method for applying signal pulses to the patient, in accordance with another example embodiment.

FIG. 14 is a flow diagram of a method 1400 for applying signal pulses to a patient, in accordance with one example embodiment. The method can be implemented by a controller or microcontroller, for example. The flow diagram 1400 can also represent functional modules or blocks, which can be state-based. The method 1400 is for controlling a functional electrical stimulation system for providing pulse stimulation to an area of a living body by way of one or more electrode leads applied to the area, the area including an associated resistance element and an associated capacitance element, wherein the electrical stimulation system includes a pulse generating circuit having a controllable output voltage to generate constant voltage pulses to the one or more electrodes, wherein the corresponding current signal of each constant voltage pulse includes a spike followed by an exponential decay to a steady state current value.

At event 1402, low voltage short series "calibration pulses" (with amplitude below 10V) are applied before the start of the treatment to measure the initial resistance of the electrode/skin. These can be, for example, non AP stimulating pulses.

At event 1404, the method 1400 determines specified target parameters for a given dosage. The target parameters may include steady state current value, pulse width, pulse frequency and duration at that steady state current value. As well, the pulse type can be specified as symmetric or asymmetric for bipolar pulses. These parameters can be retrieved from a treatment file stored in memory, or adjusted in real-time by the practitioner, for example.

At event 1406, in some example embodiments, a bipolar pulse sequence is generated. It can be presumed that the "bipolar pulse sequence" can be a pulse pair comprising one positive pulse followed by one negative pulse. For most frequencies, further processing (e.g. events 1408, 1410) may be performed between adjacent pulse pairs. Event 1406 includes controlling the pulse generating circuit to generate a constant voltage pulse having the target parameters of steady state current value, pulse width, and pulse frequency. The constant voltage pulse has a calculated voltage level which achieves the specified steady state current value to the area.

Referring to event 1408, the method includes determining the present resistance of the patient. A signal detector can be used for detecting signal parameters associated with the area of the living body, such the actual steady state current that is being applied. The applied voltage to the patient is also known or can be detected using a voltage detector. This can be used to calculate the present resistance of the patient. In some example embodiments, the present resistance can be estimated for each pulse, or periodically (e.g. one pulse in every specified number of pulses or time duration), or can be calculated as an average resistance (or moving average) over a specified number of pulses or a period of time.

At event 1410, after completion of one bipolar pulse sequence (e.g. one positive pulse followed by one negative pulse), it is determined whether the specified duration (at the target steady state current) has been completed. If not, the method 1410 returns to event 1406, wherein the next voltage level is calculated for the next bipolar pulse sequence, which accounts for any changes in patient resistance determined at event 1408. This allows the same specified target charge to be consistently applied to the patient. If the duration has completed (if "yes"), at event 1412, the next target parameters are determined for the next dosage level (target steady state current), which is again determined at event 1404.

It will be appreciated that alternative measures may be implemented in adapting control sequences and circuitry to the different embodiments, and that, without departing from the general scope and nature of the present disclosure.

Some example embodiments herein described may, for example, promote sustainable implementation and wider adoption of emerging FES applications that are presently only available as research tools given the deficiencies and drawbacks of known devices, as described above. Also, some embodiments may provide simultaneous pulses over multiple channels.

Another parameter of interest in these applications is the rise time, i.e. the slew rate of the electrical pulses, which, in general, should be as fast as possible. Namely, the relevance of providing a fast rise time in these pulses stems from the physiology of excitable tissues, namely nerve and muscle cells, and the generation of action potentials. These tissues have ion pumps that work against the delivered charge of an electrical pulse to maintain the nominal potential difference on the cell membrane. Pulses with a higher slew rate may give less time to the ion pumps to compensate for the delivered charge, allowing stimulation with lower amplitude signal. The advantages of stimulating with lower amplitude pulses may include more comfortable (i.e. less painful) therapy and a longer battery life of the device, for example.

Another consideration is that voltage activated sodium and potassium gates, that essentially generate action potentials, are triggered by a local change in the nerve membrane potential. These voltage activated sodium and potassium gates behave in a statistical fashion, i.e., each voltage gate has its own voltage level that triggers it which slightly deviates for the average trigger level. Therefore, fast delivery of charge (i.e., fast pulse slew rate) to all voltage activated sodium and potassium gates will ensure that all gates are triggered, ensuring higher success rate of generating action potentials. In the event that the charge is delivered more gradually, it is possible that a number of voltage activate gates will not be triggered. Therefore, in order to achieve more reliable response with pulses that have slower slew rate, one may need to deliver more charge, i.e., one would need to use the stimulation pulses with higher amplitude to activate critical number of voltage triggered gates. Therefore, the fast pulse slew rate has a potential to generate more reliable action potential production in the excitable tissue using less charge.

Furthermore, the device described herein in exemplary embodiments may provide improved pulse rise times and more accurate amplitude and duration control. These faster rise times may allow the potential to achieve the same tissue stimulation results with less steady-state current. This may in turn reduce the stress on the individual (i.e., perception of pain or discomfort) as well as decreases the energy consumption of the stimulator. The rise time, in combination with the accurate amplitude and duration control also may provide that over time no charge will be built up in stimulated tissues, which can be an important aspect for FES applications, especially for applications involving implanted FES systems.

In some embodiments, the slew rate of the pulses produced by the herein described systems and designs are significantly faster than the 1 μs slew rates common to some existing devices and systems. For example, in one embodiment, a pulse slew rate of no more than 500 ns is achieved. In accordance with another embodiment, a pulse slew rate of no more than 100 ns is achieved. In accordance with yet another embodiment, a pulse slew rate of no more than 8 ns is achieved. In accordance with yet another embodiment, a pulse slew rate of no more than 5 ns is achieved. In accordance with yet another embodiment, a pulse slew rate of no more than 2 ns is achieved. In accordance with yet another embodiment, a pulse slew rate of no more than 10 ns is achieved. Accordingly, the pulse slew rates may, in some embodiments, be as much as two orders of magnitude faster than conventional systems.

In one embodiment, the provision of such improved pulse rise times may also or alternatively allow for a reduction or minimization of physical discomfort experienced by a patient as a result of the pulse stimulation. For example, by applying a reduced charge to the stimulated tissue, or again by achieving greater tissue responsiveness, treatments implemented using the herein described device may reduce, if not completely avoid patient discomfort.

As will be appreciated by the skilled artisan, the highly flexible architecture of the above-described embodiments and below-provided examples may be particularly suitable for the implantation of battery-powered external functional electrical stimulators (FES) and neuroprostheses, and readily amenable to emerging sophisticated FES applications, such as closed-loop controlled and brain machine interfaced neuroprostheses, for example, as well as various other applications.

Figure 23:
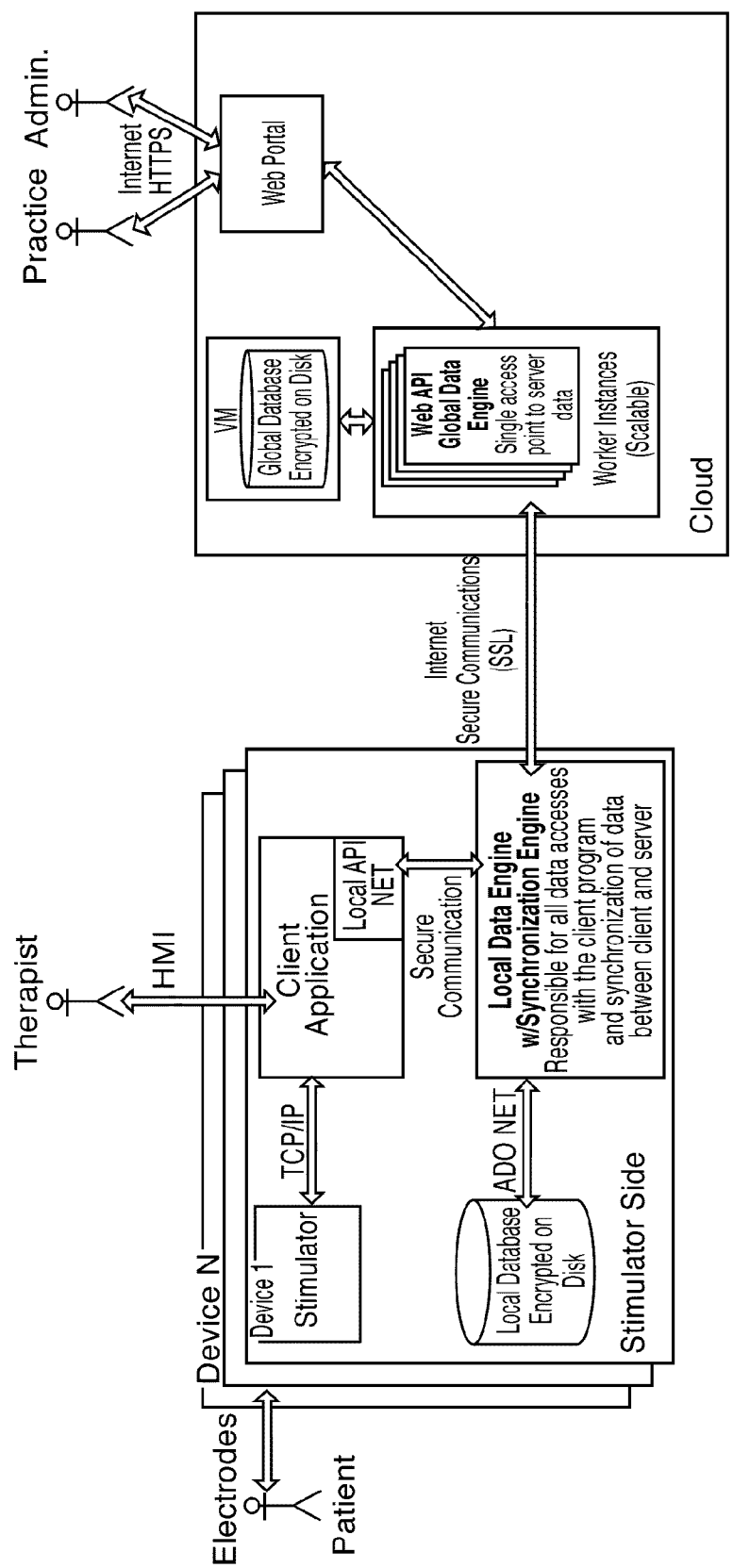
FIG. 23 is an example high level diagram of a communication system for one or more FES systems, in accordance with an example embodiment.

Reference is now made to FIG. 23, which shows is an example high level diagram of a communication system for one or more FES systems, in accordance with an example embodiment. The system design incorporates multiple subsystems that together create the required components for the administration and delivery of FES therapy to patients. As shown in FIG. 23, there can be three main subsystems as part of the overall system; Stimulator, Local Interface, and Backend Data Management System (BDMS).

The Stimulator System is a system which is used to provide stimulation treatment (protocol) to a patient. The main components of the system are an ARM7 Microprocessor, the software running on the ARM7 (stimulator application), as well as custom electronics and physical electrodes which interface between the ARM7 and the human body. The stimulator application calculates the appropriate stimulation level based upon the protocol type and transmits this analog output to the human body via the connected electrodes.

The Stimulator application is command based and event driven. Its main function is to listen for commands, decode these commands, and execute them accordingly. As a result, the Stimulator device can be controlled by another application if it can establish a valid communication path and send the correct commands as defined by the Application Programming Interface (API) for the device.

The local interface is the primary interface used by the therapist to configure, setup and administer the actual treatment, including user interface to view data and control the system. This subsystem will interface to the stimulator to administer the actual treatment protocols as well as the Backend Data Management System to manage patients, prescriptions, therapists as well as synchronize treatment details between multiple devices in a practice.

The Backend Data Management System is used to manage the overall treatment process including Device ID's, Therapist ID's, Patient IDs (PUID's), prescriptions and primary report interface. This cloud-based system can also allow for synchronization between multiple devices in the field. Access to patient data can be made over secure Internet connections and other communication mediums through the Backend Data Management System.

In accordance with some example embodiments, the FES system can be used to assist with the "bioinfomatics" use of the device and the patient receiving treatment. For example, the system can be used for capturing, in memory, information of the pulses applied during treatment, sending to a central repository (e.g. Backend Data Management System), and providing this information from the central repository to one or more of patients, clinicians, clinics, administrators, third party payors, and other information relating to the patient, treatment or use of the system. The information can be used to determine, automatically or manually, best protocols or treatment options based on prior results such as successes and failures.

Many government and private insurance programs are under increasing pressure to limit healthcare expenditures and are adopting various measures to control costs. These measures include, but are not limited to healthcare reform measures, pay-for-performance, Comparative Effectiveness Research, and group purchasing. Increasingly, third party payers are converging on a set of common criteria in the assessment of whether a technology improves health outcomes such as length of life, quality of life and functional ability.

Insurers generally seek evidence that a new therapy represents an efficient use of healthcare resources. Ongoing clinical studies and the aggregated database of patients that have been prescribed patient "keys" will capture and provide the data to support reimbursement.

This assists with payment by health care systems. There is increasing pressure on hospitals to discharge patients more rapidly and preferably to discharge them to their homes. Patient discharge from in-patient rehabilitation hospitals is determined by a number of factors, including the attainment of certain functional independence goals.

In another aspect, the system can be used to provide a method for prescribing a treatment to a patient. For example, the system can be used for receiving a "prescription" purchase request, and providing a patient dedicated electronic key in response to the purchase request. The electronic key can include: access to protocol(s) for a prescribed therapy intervention; a record of the pattern of use of the protocols, including at least duration, frequency and amplitude of pulses to be applied to the patient; outcomes captured during treatment; and reports on progress and treatment planning.

Figure 24:
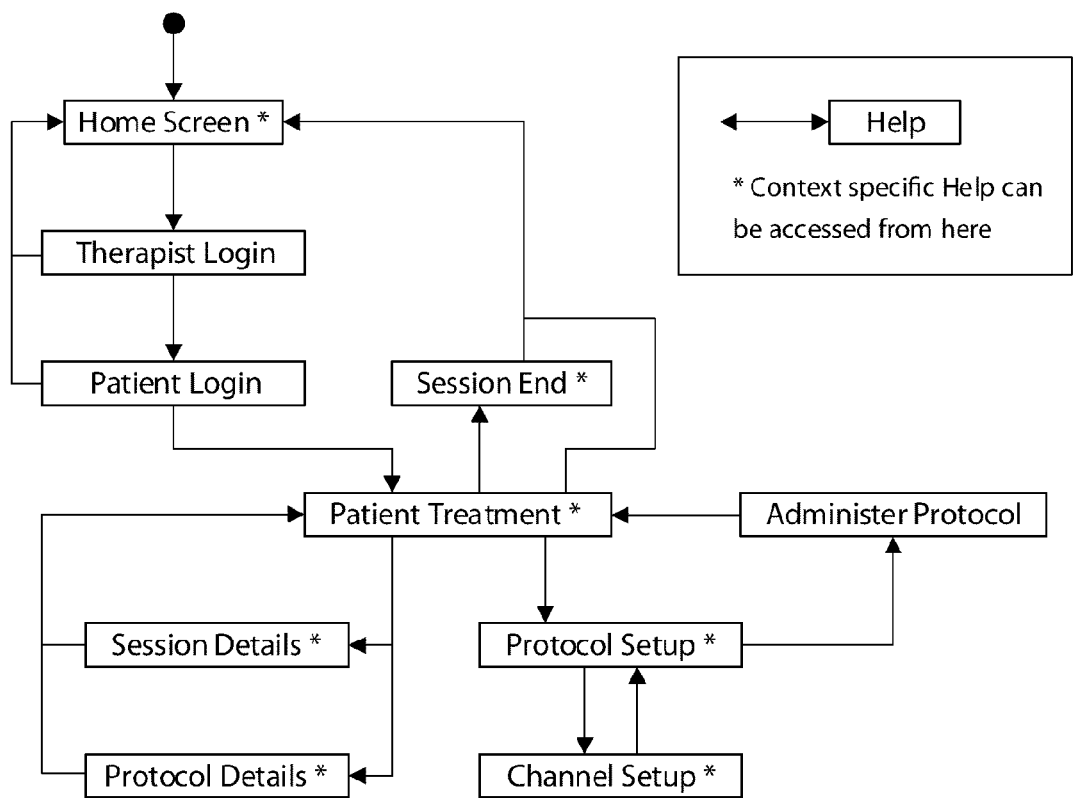
FIG. 24 is an example flow diagram of user interface screens on a computer device for controlling and managing an FES system, in accordance with an example embodiment.

FIG. 24 is an example flow diagram of user interface screens on a computer device for controlling and managing an FES system, in accordance with an example embodiment. The graphical user interface on the clinical based workstations and portable stimulator devices will be direct users to protocols, diagnostics that report patient progress, and/or instructional material including videos, help menus and user manual.

Referring to FIG. 24, the home screen is presented to the user upon successful start of the application. The home screen presents the following navigation choices: Patient Treatment, Settings, and Help. The home screen also displays the current stimulator device battery level, therapist login, and patient login may be implemented using identifiers and passwords. Referring to the Therapist Login screen, after selecting Patient Treatment on the Home Screen the Therapist Login screen will be displayed prompting for the keyed entry of a Therapist ID and password. Once the OK Button is pressed the UI task will take the entered values of the Therapist ID and Password and query the database for validity. If the Cancel Button is pressed the UI will return to the Home Screen. Once the Therapist logs in, the User Interface will prompt the user for a Patient ID (PUID). The device again queries the database for validity once the OK button is pressed. If the Cancel button is pressed the UI returns to the Home Screen.

Figure 25:
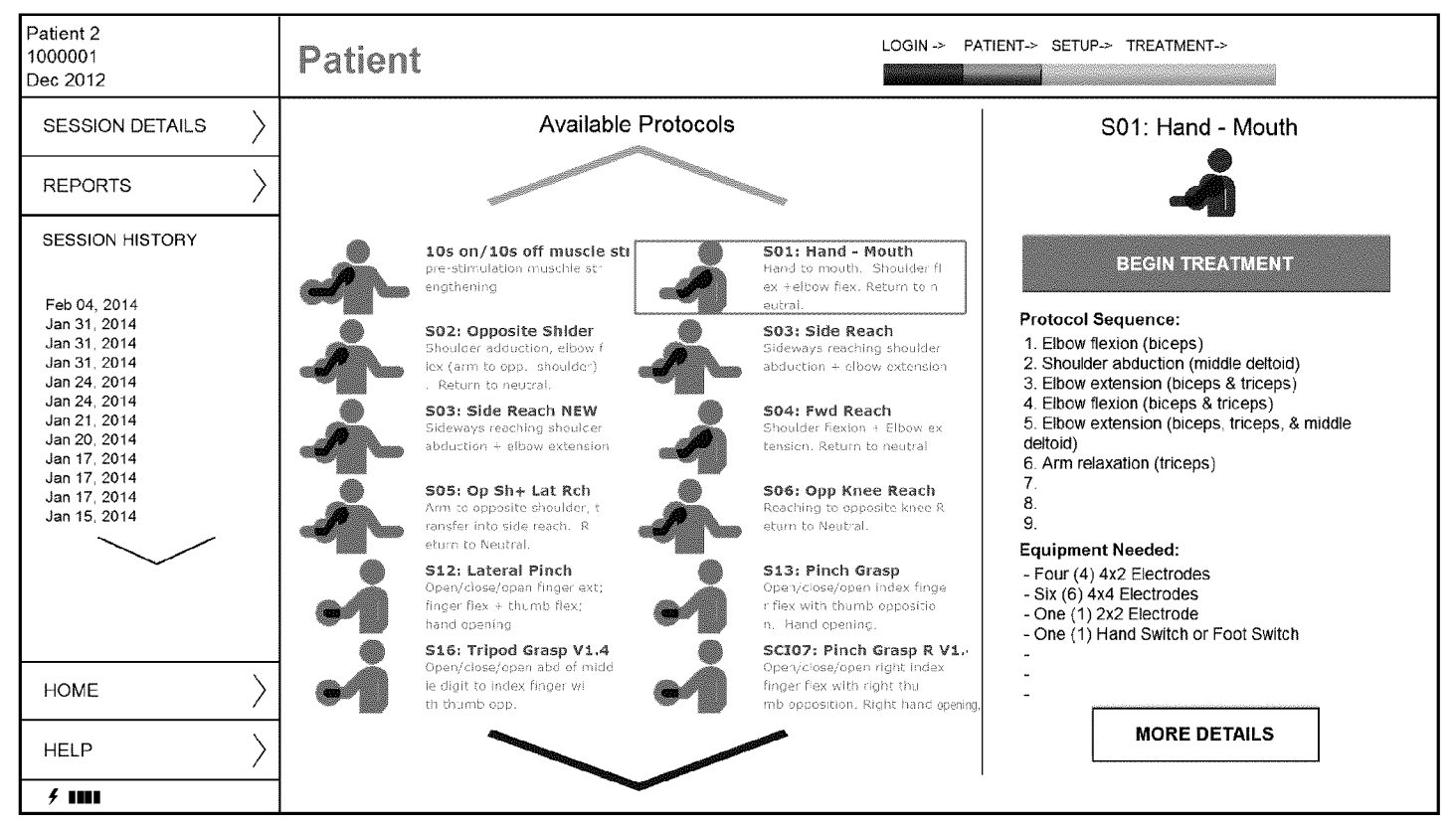

Once logged in, various example screenshots of the user interface screens in FIG. 24 are illustrated in FIGS. 25 to 31. After successful Therapist and Patient login, the UI displays the Patient Treatment Screen, for example as illustrated in FIG. 25. In the Patient Treatment Screen the following information is displayed: Patient Identification; Session History; Available Protocols; Selected Protocols; and Stimulator Battery Level.

The Patient Identification data is displayed on the screen, for example at least patient name (sometimes first name only) and birth date. The Session History for the patient is a list of previous session dates associated with the selected Patient ID. The Session History is from the database and includes the times of previous sessions. Each date can be selected by the use through the user interface, for example, resulting in FIG. 26.

The Available Protocols is a display of Protocols which are available to the Patient, and is presented to the user through the user interface. The example protocols shown include 10 second on/10 second off muscle strengthening, Hand-Mouth, Opposite Shoulder, Side Reach, Side Reach NEW, Forward Reach, Opposite Shoulder and Lat Reach, Opposite Knee Reach, Lateral Pinch, Pinch Grasp, Tripod Grasp, and Pinch Grasp variation.

The Selected Protocols is a display of Protocols (stimulation parameters) which have been selected for the current treatment session. These are typically selected by dragging and dropping from the Available Protocols. The example selected protocol shown in FIG. 25 is a Hand-Mouth protocol sequence.

Figure 26:
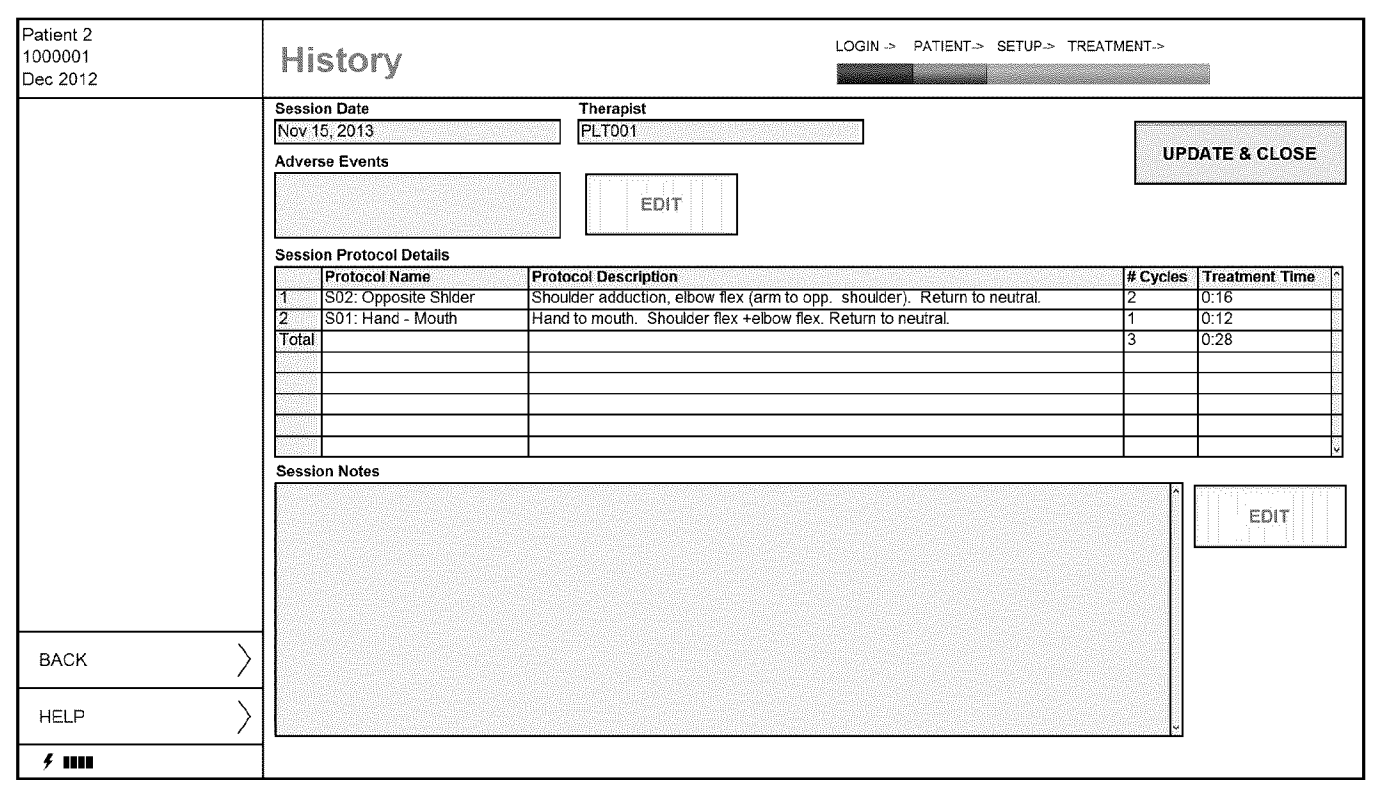

FIG. 26 is an example user interface screen for Session Details. The Session Details Screen displays information from a past session (e.g. selecting a particular session date from FIG. 25). It displays the following information: Protocols Used During Session; Number of Cycles; Total Treatment Time; Individual Protocol Time; Session Notes; Stimulator Battery Level; and Pulse Amplitude Per Channel. At least some or all of the information in the Session Protocol Details can be automatically populated, based on the system performing the particular protocol(s), in some example embodiments. The user or practitioner can also edit some of the fields, including the Adverse Events and the Session Notes to annotate such information, for example. More or less information may be displayed, in other example embodiments.

Figure 27:
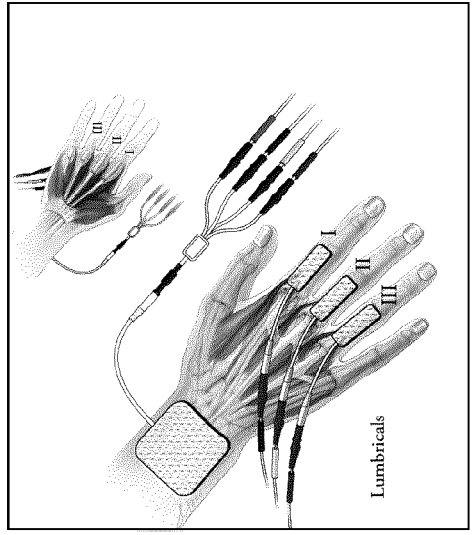
FIG. 27 is an example user interface screen displayed on a computer device for protocol details, in accordance with an example embodiment.

FIG. 27 is an example user interface screen for Protocol Details, in accordance with an example embodiment. The Protocol Details provides a text-based description of the protocol, a selectable list of the Channels and a viewing window for relevant image or video files. Images and/or videos are displayed in the viewing window when a Channel button is clicked. As shown in FIG. 27, the images can include anatomical images for electrode placement for each protocol. The example shown in FIG. 27 is an image of the Lumbricals, and the applicable electrode placement. This provides visual confirmation and verification to the practitioner of the particular protocol being implemented, for example. Selection of any specific channel results in the user interface of FIG. 29 being displayed.

Figure 28:
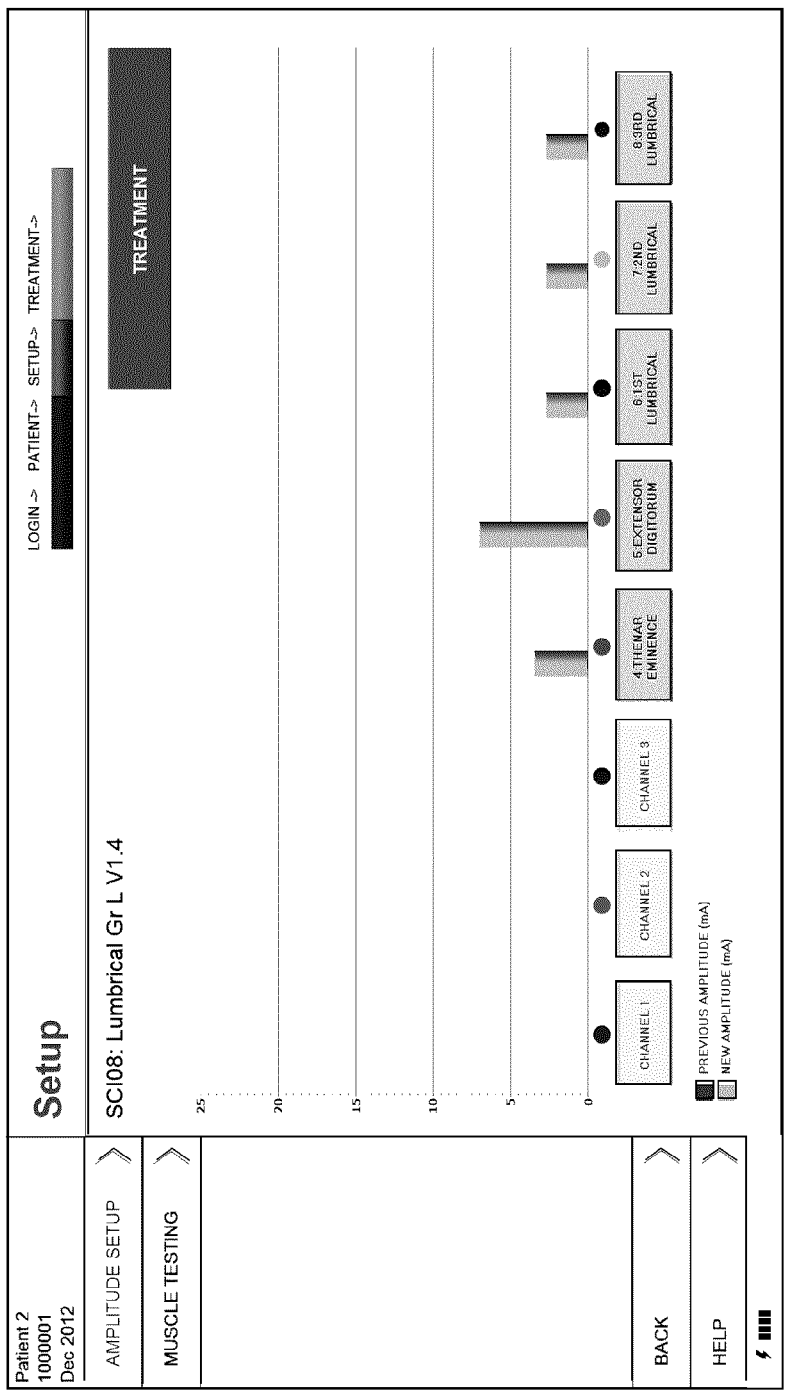
FIG. 28 is an example user interface screen displayed on a computer device for protocol setup, in accordance with an example embodiment.

FIG. 28 is an example user interface screen for Protocol Setup, in accordance with an example embodiment. The Protocol Setup allows the user/practitioner to modify the default setup of the max values per channel. The user does this by selecting the channel to adjust and then moving the sliders up and down with the respective controls. The user has the ability to select 1 Hz or 40 Hz stimulation train while he/she is adjusting the stimulation amplitude (per channel). 1 Hz stimulation train is typically used to determine if there is a muscle response at all, and 40 Hz stimulation trains are typically used to determine the stimulation intensity needed for the muscle (i.e., stimulation channel) of interest. The user can also start the selected protocol.

Figure 29:
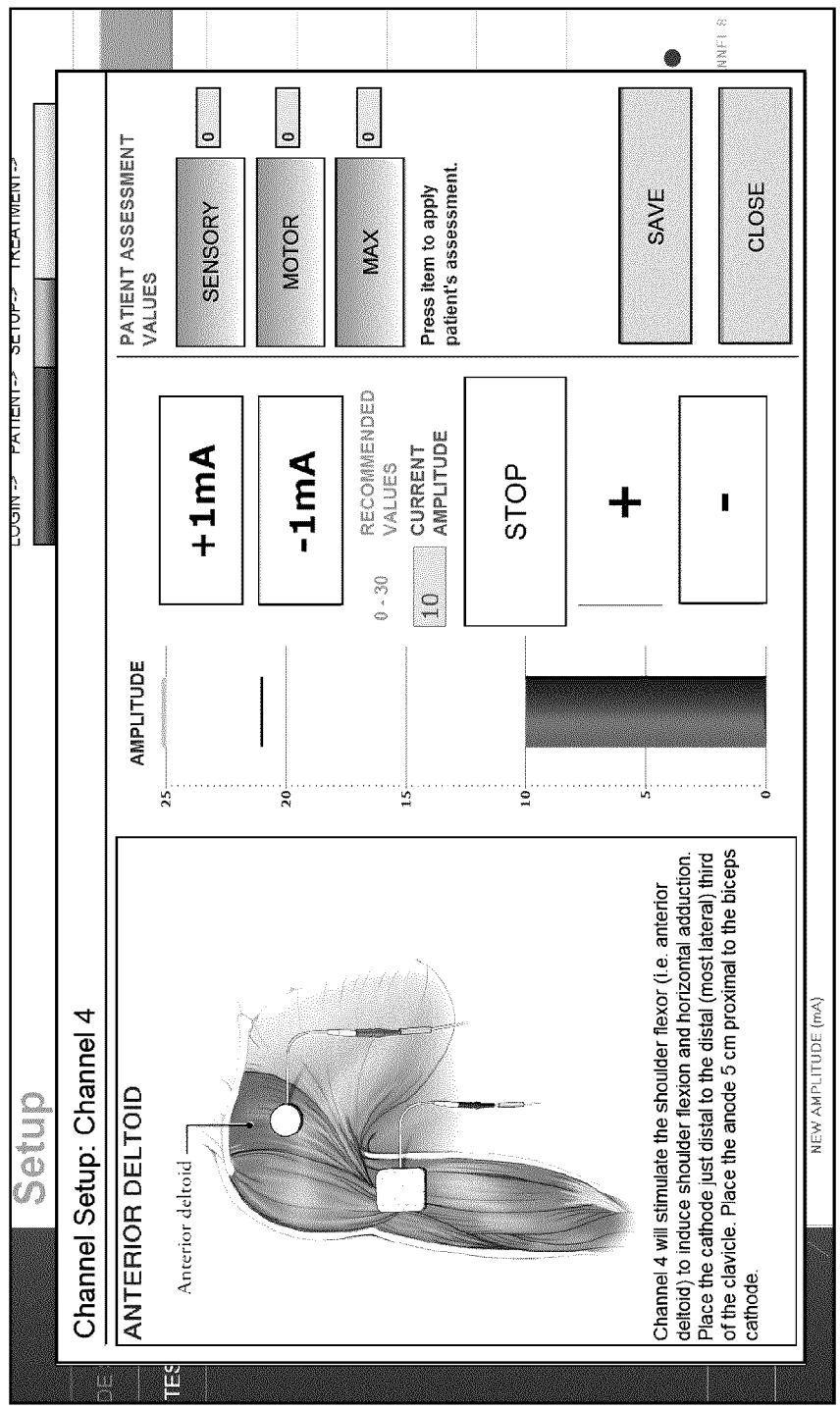
FIG. 29 is an example user interface screen displayed on a computer device for channel setup, in accordance with an example embodiment.

FIG. 29 is an example user interface screen for channel setup, in accordance with an example embodiment. For example, this screen may be accessed by selecting a channel from FIG. 27. The Channel Setup allows the user to slide the bar within the max or min values per the selected channel via touching an sliding the bar or using Up and Down Buttons. The user will additionally be able to save in memory (and/or to the database) the following values:

Sensory—the first level that is registered by the patient;
Motor—the level where contraction starts;
Max—the level where max contraction occurs, or where it is too painful for the level to increase; and
Treatment amplitude—the level used for treatment.

Figure 30:
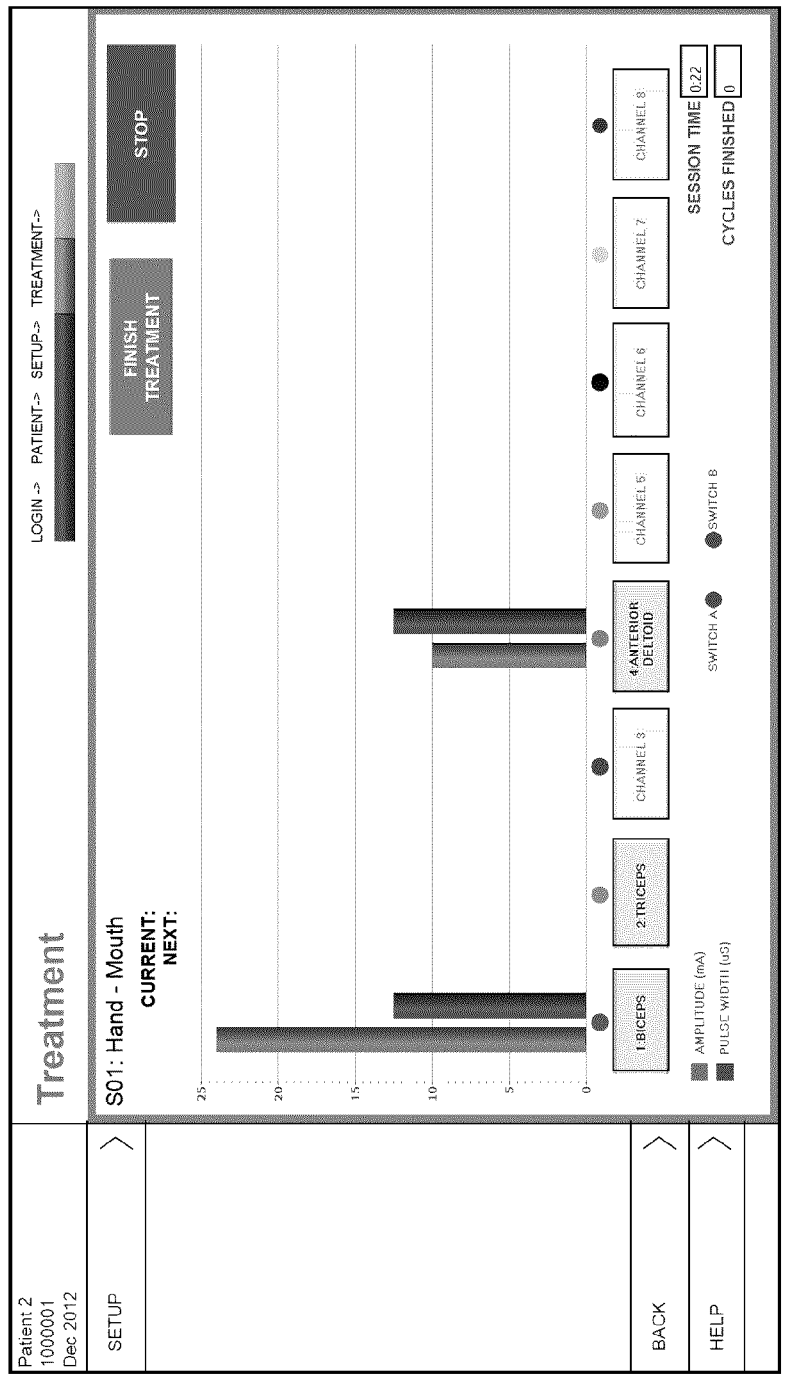
FIG. 30 is an example user interface screen displayed on a computer device for administer protocol, in accordance with an example embodiment.

FIG. 30 is an example user interface screen for Administer Protocol, in accordance with an example embodiment. The Administer Protocol displays the number of cycles and the total elapsed treatment time along with the amplitude, pulse duration and frequency for each channel. If a Protocol is paused or stopped, the user has the ability to resume the protocol from this screen. The control menu can include user selectable options for Help, Pause/Start, Stop, Setup and Home.

The "Setup" button brings the user to the Setup Protocol User Interface (FIG. 28). The "Pause/Start" button pauses/stops the treatment and allows for the user to modify the Protocol settings until the user returns to the administer protocol page.

Figure 31:
FIG. 31 is an example user interface screen displayed on a computer device for session end, in accordance with an example embodiment.

FIG. 31 is an example user interface screen for Session End, in accordance with an example embodiment. The Session Protocol Details are typically automatically updated based on the protocol that was just performed. The Session End screen gives the user the ability to record any adverse events, reasons why treatment was stopped, and notes when a Protocol(s) is stopped. The adverse events and reason why treatment stopped may include dropdown menus and/or checkboxes of predefined reasons. The user records may also be timestamped, for example to accord with governing policies and regulatory practices. If multiple protocols were used then details for each protocol may be recorded by the user.

One example provides results an exemplary FES therapy process for improving brain and associated muscle function in individuals suffering from a neuromuscular deficit, which process provides an example only of the various FES applications, methods and treatments that may be facilitated by the above-described FES devices and systems. In this example, the individual was suffering from the neurological disorder following a stroke. It will be appreciated that this kind of neurological disorder of the central nervous system may have resulted from stroke, spinal cord injury, brain injury, multiple sclerosis, and any other injury both traumatic and non-traumatic to the central nervous system, for example.

Individual Description: The individual was a 22-year-old woman who suffered a hemorrhagic stroke in the right frontal parietal area two years prior to the participation in this study. The individual presented at an individual rehabilitation centre with motor recovery status scored by CMSMR (Chedoke McMaster Stages of Motor Recovery) as follows: arm=1, hand=2, leg=2, and foot=2. After four months of rehabilitation, the CMSMR scores were as follows: arm=2, hand=2, leg=4, and foot=2. While left leg showed some recovery, the left arm was not functional. At the beginning of the FES-mediated protocol, the individual was independent in activities of daily living with the help of cane and ankle-foot orthosis, but reported that she rarely, if ever, used her paretic upper limb. Movement of the upper extremity was characterized by a flexor synergy pattern. The individual had increased resistance to passive stretching in the distal flexor musculature. Tactile sensation was shown not to be severely impaired throughout the upper limb by the use of the two point discrimination test. Stroke patients, such as the individual of the instant study, are considered neurologically stable and do not show any signs of further improvement 24 months following stroke. Therefore, the individual recruited to this study was in the chronic phase of injury, 24 months post stroke, was severely disable as measured by CMSMR and was not expected to improve regardless which therapy is provided to her.

Figure 15:
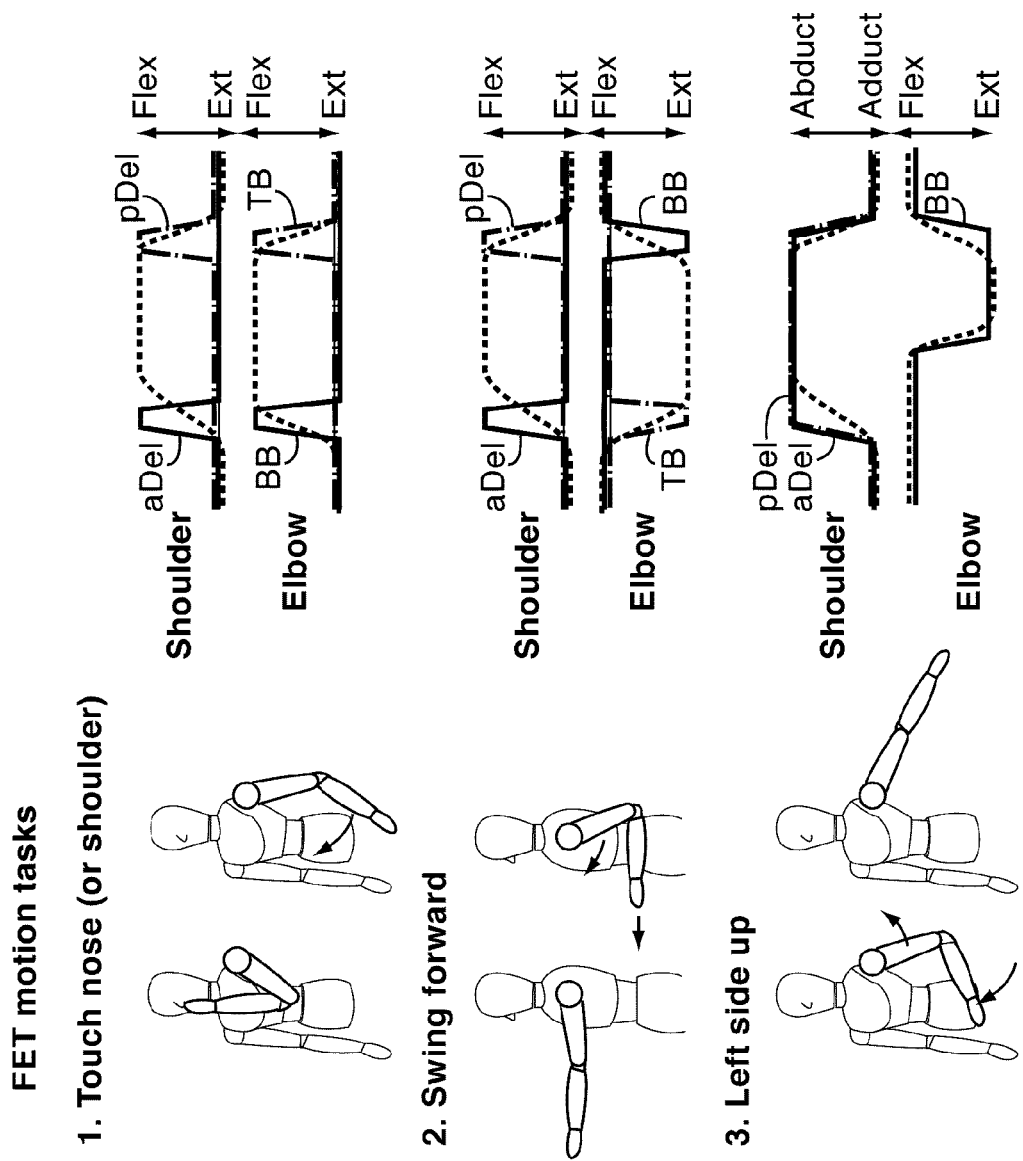
FIG. 15 is a schematic picture of functional motion tasks conducted, and of shoulder and elbow joint angle changes and stimulus pattern of each muscle where thick and thin lines indicate joint motion and stimulus pattern (timing of ON/OFF)

Functional electrical stimulation therapy: An FES-mediated protocol was delivered by way of an electric stimulator (electrical stimulator used was a prototype of the electrical stimulator discussed above), with standard self-adhesive surface stimulation electrodes. In the study the following muscles were stimulated with the surface stimulation electrodes (the locations of the electrodes for each muscle are shown in the FIG. 15): anterior (aDel) and posterior deltoid (pDel), biceps brachialis (BB) and triceps brachialis (TB), extensor carpi radialis, extensor carpi ulnaris, flexor carpi radialis, and flexor carpi ulnaris. Stimulus parameters used to stimulate the nerves that are innervating the muscles of interest were asymmetric bipolar current pulses with the pulse duration of 250 μsec and frequency 40 Hz. During the protocol the stimulus was delivered to the muscles of the paralyzed limb in such a way that these muscles produced movements that accurately mimicked the movements that the brain would produced if the patient were not paralyzed. When the stimulus was delivered to the muscles, it was gradually increased or decreased (instead of being delivered instantaneously) using ramp up and ramp down functions lasting from 0.5 to 2 seconds. The therapist used a hand switch to trigger stimulation when he determined that the individual needed assistance with the task.

FES-Mediated Protocol: Briefly, the FES-mediated protocol consisted of pre-programmed coordinate muscular stimulation and manual assisted (externally generated) passive motion to establish physiologically correct movement. During the movement, the individual was asked to imagine the movements and to try to carry it out herself. At the beginning of the study the patient was unable to move the arm voluntarily and therefore was not able to physically execute voluntarily imagined movements. The FES was delivered to shoulder, elbow, wrist and finger extensor and flexor muscles, while the individual (assisted by the therapist) performed the following types of motions: (1) touch nose, (2) touch shoulder, (3) move arm forward, (4) lift arm left side up, (5) reach and grasp large objects, (6) reach and grasp small objects, (7) manipulate objects during grasp, and (8) place the object at a designated location and release the object. The FES-mediated protocol was carried out for an hour. The protocol, at a minimum, comprises 40 one-hour sessions wherein at least 3 one-hour sessions are delivered per week, however the protocol may be repeated more frequently, if desired. In case of the individual of the instant example, the protocol was preformed twice daily. In individuals who have suffered a stroke, the neuromuscular recovery typically starts proximally followed by the recovery of the distal neuromuscular compartments. Therefore, the FES-mediated protocol began by training shoulder and upper arm muscles first, followed by wrist and fingers training.

TABLE 1

Figure 16:
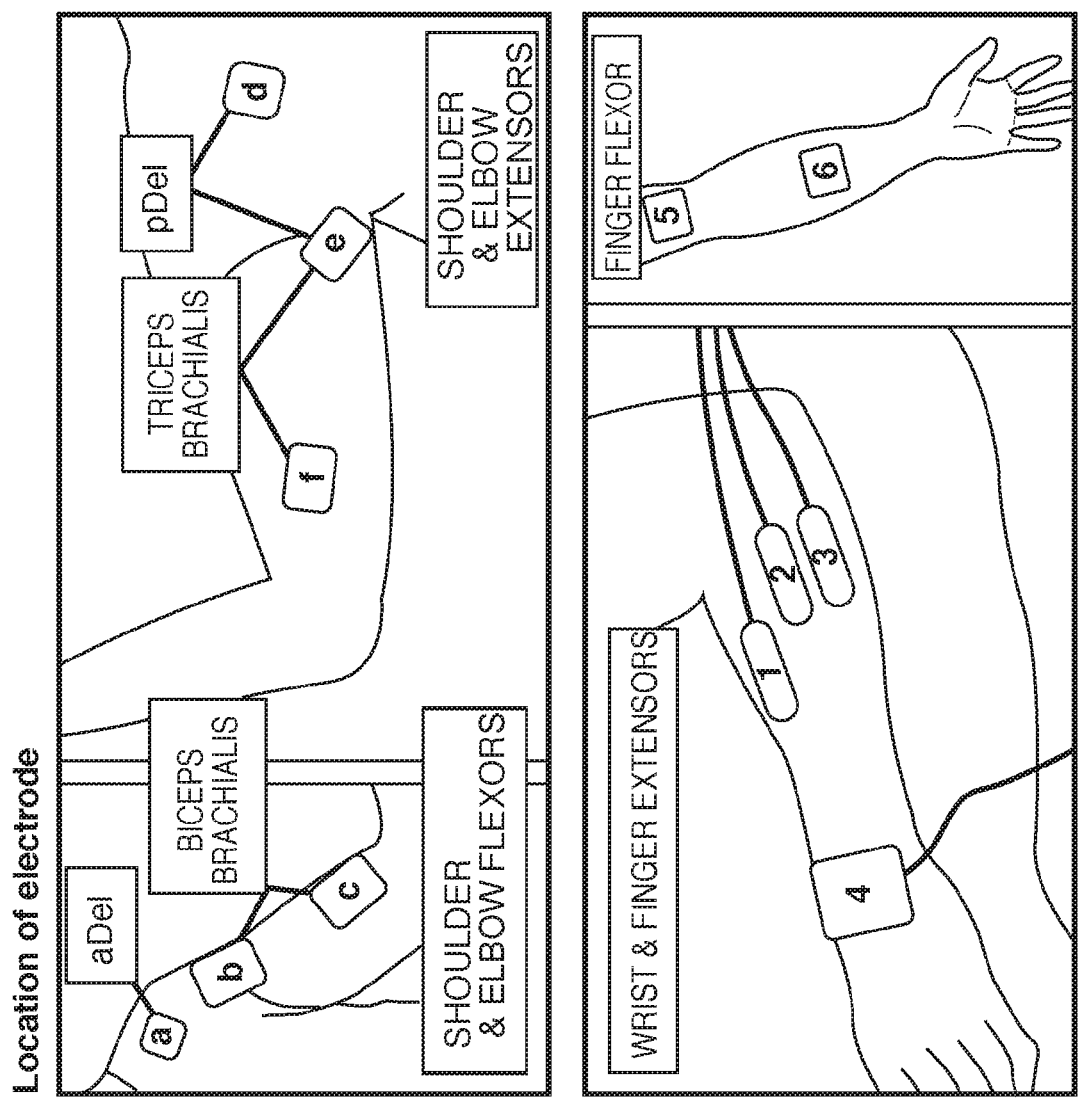
FIG. 16 is a schematic depiction of electrode locations.

Upper limb motion tasks, types of motion, and electrodes used for in each task. The alphabetical characters and numbers in this figure match to those in the FIG. 16.

| SHOULDER & ELBOW MOTION | | | | |
|---|---|---|---|---|
| Task | Shoulder motion | (Electrode) | Elbow motion | (Electrode) |
| Touch nose | Flexion | a-b | Flexion | b-c |
| Touch shoulder | Flexion&Int. rotation | a-b | Flexion | b-c |
| Swing forward | Extension | d-e | Extension | e-f |
| Left side up | Abduction | a-b & d-e | Extension | e-f |

| WRIST & HAND MOTION | | |
|---|---|---|
| Task | Target motion | (Electrode) |
| Bottle grasping | Wrist extension & full finger open | 1-4, 2-4 & 3-4 |
|  | Finger flexion | 5-6 |
| Small object picking | Two finger (thumb & index) open | 1-4 |

During the FES-mediated protocol, a therapist controlled/triggered the arm movements using a pushbutton. During the movements, the physiotherapist guided the arm and assisted the individual with the neuroprosthesis in performing the desired task. This assistance provided that all movements were carried out in a correct physiological way, i.e., neuroprosthesis induced movements did not oppose natural joint movements and respected the anatomy of bone and soft tissue composition. In the early stages of the treatment, the arm tasks were performed by the combination of muscular stimulation and therapist's assistance. As the individual improved, the assistance was reduced to the necessary minimum. Typically, the stimulation protocols were adjusted weekly or biweekly. The individual was asked to repeat the same arm task 10 times for each motion during a single treatment session. The treatment sessions lasted up to 60 minutes.

Outcome Measures—Clinical assessments: CMSMR and Motricity Index tests for the upper limb were used to assess the arm and hand functions. The degree of spasticity in the affected upper limb was evaluated using the five-grade Modified Ashworth Scale (MAS).

H-reflex and M max: To assess the excitability of the spinal motoneuron pool in the flexor carpi radialis (FCR) muscle, the Hoffman reflex (H-reflex) was elicited. The H-reflex was evoked by stimulation of the left median nerve with a monopolar electrode placed in the inside of cubital joint. A rectangular pulse (1 ms) was generated by a constant voltage stimulator (DPS-007, Dia Medical System Co., Japan) that was triggered once every 5 s.

Maximal voluntary contraction (MVC): The electromyographic (EMG) signals in the following paralyzed upper arm muscles were detected by a bipolar differential amplifier (Bortec AMT-8; Bortec Biomedical, Canada): aDel, pDel, BB, TB, flexor capiradialis (FCR), extensor digitrum longus (EDL), and first distal interosseous muscles (FDI). A pair of surface electrodes (BiPole; Bortec Biomedical, Canada) was placed along the muscle fibers over the belly in each muscle with an inter-electrode distance (center to center) of 10 mm. The recorded EMG signals were amplified 500 times and digitized at a sampling rate of 1,000 Hz over a period of 500 ms before and 500 ms after the onset of the movement.

Active range of motion test: The individual was asked to move her arm toward following five directions as much as she could: (1) forward, (2) backward, (3) upward, (4) right side, and (5) left side. During the movements, we recorded the position of the shoulder, elbow, and wrist joints, and the second joint of index finger. The individual did three trials for each of the five movements.

Circle drawing test: This test was aimed to assess the ability to coordinate shoulder and elbow joints. During circle drawing, the subject requires the ability to coordinate shoulder and elbow movements. Specifically for individuals whom have suffered a stroke who have spasm in their elbow joint it is not easy to draw a wide and a properly shaped circle. The position of the shoulder, elbow, and wrist joints, and the second joint of index finger while the individual drew the circle on a table was recorded. During the assessment the movements were self-paced, and the task continued for 30 seconds.

Originally, it was planned to assess the individual using tests "Outcome Measures—Clinical assessments", "H-reflex and M max", and "MVC". However, during the first 6 weeks of training the individual surprisingly showed remarkable improvement of her shoulder and elbow function, thereby prompting the addition of tests "Active range of motion test" and "Circle Drawing Test" to further evaluate functional motion of the upper limb.

Figure 20:
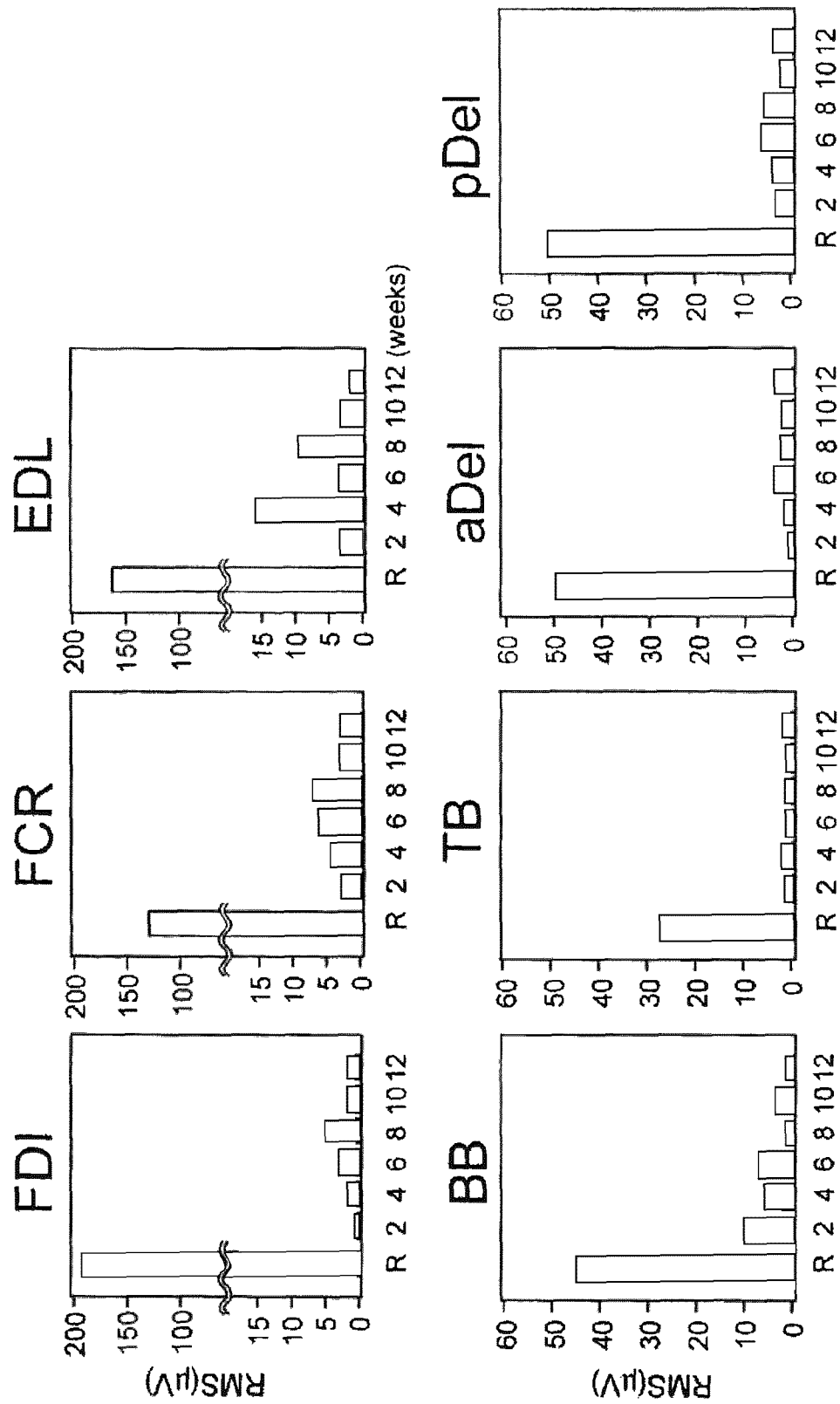
FIG. 20 is a graph of a time course showing changes of a maximal voluntary contraction level of the first distal interosseous muscles (FDI), flexor capi radialis (FCR), extensor digitorum (EDL), biceps brachialis (BB), triceps brachialis (TB), anterior (aDel) and posterior deltoid (pDel) muscles compared to the unaffected side arm as a reference.

Results: The individual successfully completed all training sessions and assessments. Following 12 weeks of FES-mediated protocol, the individual was able to pick a thin object, touch her nose and draw circles, for example, tasks which could not be accomplished prior to the FES-mediated protocol sessions. As the clinical measures selected, namely the CMSMR and Motricity Index tests are coarse measures, these tests did not show changes in the scores following the 12-week protocol. However, the MAS of the hand and wrist showed reduction in spasticity over the course of the training (wrist: 3 to 2, hand: 4 to 3). H-reflex, which reflects the spinal motoneuron excitability, also showed remarkable reduction with training (FIGS. 17 to 19). Namely, the size of the H-reflex was quite high at the beginning of the protocol (82.09% Mmax) and as the time passed it decreased considerably (53.65% in $6^{th}$ week and 45.04% in $12^{th}$ week), indicating that the high tone which is commonly associated with the damaged to the supra spinal compartments of the central nervous system is reverting, and that the central nervous system function is returning back to its normal levels of tone and reflex responses. FIG. 20 shows the changes in the MVC in the upper arm muscles obtained every two weeks. The MVC levels in all muscles measured were at "zero" during the baseline assessment. In other words, the patient was unable to activate a single muscle in the affected arm voluntarily. As the protocol progressed the patient gained ability to voluntarily activate the muscles and further improved with continuation of the protocol. It is worth mentioning that the MVC levels in the affected arm were remarkably smaller than that of the unaffected arm. However, even the low levels of MVCs were sufficient to allow the patient to effectively and voluntarily move the arm and fingers to reach and grasp objects. A good example of the muscles which showed considerable improvement following the FES-mediated protocol are the FDI and TB muscles, which did not show any EMG (RMS μV) activity at the baseline and following the FES-mediated protocol showed remarkable improvements in voluntary EMG and muscle contraction control. Table 2 shows the shoulder and elbow dynamic range of motion. It is clearly shown that the value of dynamic range of motion for the shoulder and elbow joint at week 12 showed remarkable improvement as compared to those measured at week 6. At week 0 the individual did not have any voluntary movement in the affected arm. Therefore, transformation from no movement in week 0, to restricted movement in week 6 followed by much more expanded range of motion in week 12 is a remarkable change. Given that the individual of this study was in the chronic injury phase, as noted above, and therefore not expected to show improvement regardless whether any intervention was provided, the changes observed and noted herein are remarkable. Furthermore, such changes have not been previously observed in chronic severe stroke patients.

TABLE 2

| | Dynamic range of motion (rom) of the shoulder and elbow joints. | | | | | | | | | |
|---|---|---|---|---|---|---|---|---|---|---|
| | Shoulder | | | | | | | | Elbow | |
| | Flexion | | Abduction | | Int. rotation | | Ext. rotation | | Extention | |
| Direction of Motion | 6th wk (deg) | 12th wk (deg) | 6th wk (deg) | 12th wk (deg) | 6th wk (deg) | 12th wk (deg) | 6th wk (deg) | 12th wk (deg) | 6th wk (deg) | 12th wk (deg) |
| Forward | 19.82 | 28.77 | 31.25 | 31.77 | | | | | 74.90 | 75.36 |
| Upward | 34.81 | 44.25 | 55.22 | 62.63 | | | | | 100.78 | 112.67 |
| Left side | | | 32.51 | 40.47 | | | 22.74 | 31.84 | | |
| Right side | 52.19 | 47.35 | | | 83.47 | 108.70 | | | | |

FIG. 21 shows the x-y plot of the shoulder, elbow, wrist, and index finger positions while the individual was performing circle drawing test. The absolute coordinates of individual joints were represented in the upper three figures in FIG. 21. The joints and index finger coordinates with respect to the shoulder joint coordinate frame (i.e., assuming that the reference coordinate frame is in the shoulder joint) are shown in the bottom three figures in FIG. 22. While the size of drawn circle by the index finger was small at the 6th week of the FES-mediated protocol, its size became larger as the protocol progressed. At week 0 the individual do not have any voluntary movement in the affected arm and was unable to drawn circles.

The purpose of this study was to assess the effect of 12 weeks intensive FES-mediated protocol on a chronic severe stroke individual (CMSMR score 2 or less). Although motor capacity score, i.e., CMSMR and MVC tests did not show any significant changes, due to the courses of the tests, the MAS and the amplitude of H-reflex were reduced as the result of the FES-mediated protocol. Additionally, the kinematic results showed a profound improvement in the ability to perform arm movements and to coordinate shoulder and elbow joints. These results suggest that the improvement of the upper arm functional motion can be attributed to retraining of the central nervous systems through means of neuroplasticity, which is observed in improvement of the upper limb voluntary motor function as well as the reduction of muscle tone and/or spasticity.

Traditionally neuromuscular electrical stimulation has been used to increase strength of the voluntary muscle contractions in various neurological patients and healthy individuals. But recent applications of electrical stimulation are shifting the focus from muscle strengthening towards re-training the central nervous system and improving motor control of the stroke individuals. In this study, FES-mediated protocol was used to retrain a chronic stroke individual to voluntarily perform coordinated multi-joint movements with the arm that was previously paralyzed as a result of stroke. Since the stimulus intensity we used was approximately two times larger than the motor threshold, one could not expect that the FES-mediated protocol generated changes in muscular function due to an associated increase in muscle strength. This assumption was confirmed by the results shown in the FIG. 20, that is, there were no consistent changes of the MVC in the upper limb muscles.

At the beginning of the FES-mediated protocol, the individual's upper limb had high muscle tone. However, the muscle tone of wrist and elbow flexors was remarkably decreased as the result of the FES-mediated protocol, which was clearly reflected by the results of MAS (Table 1) and H-reflex (FIG. 20). This result was in good agreement with the previous findings that describe the effects of the electrical stimulation on the reduction of the abnormally high muscle tone. It should be noted that the resting condition of the individual's arm, specifically hand, was drastically changed with the time course of training. Namely, the individual was able to relax her hand and keep the hand relaxed during reaching motion. Therefore, the improvement of the upper arm functional motion can be partly attributed to the reduction of muscle tone and/or spasticity. This finding supports the classical concept that muscle tone reduction represents simplistic solutions to the deficit in motor control after stroke.

Pre-programmed stimulus patterns were developed that are able to generate variety of upper limb movements/functions. The temporal activations of the muscles induced by the FES were similar to those of intact neuromuscular system that is performing the same task, i.e., the muscle activations were designed to clone actual natural movements. Thus, during the movements the individual could feel when she was supposed to activate muscle contractions and how to sequence them to produce desired movements. The fact that marked changes in the H-reflex were observed and that a number of muscles that the individual was unable to voluntarily contract prior to the FES-mediated protocol were under her voluntary control at the end of the protocol suggests that the functional improvements induced by the FES-mediated protocol are in part due to changes that occur in the central nervous system. In other words, the intensive, repetitive and yet diverse FES-mediated protocol may be promoting plastic reorganization of the central nervous system. Therefore it is predicted that the following mechanism may cause the changes observed. If a hemiplegic individual who strains to execute a task is assisted with the FES to carry out that same task, he/she is effectively voluntarily generating the motor command (desire to move the arm, i.e., efferent motor command) and the FES is providing the afferent feedbacks (afferent sensory input), indicating that the command was executed successfully. Therefore, it is believed that by providing both the motor command and sensory input to the central nervous system repetitively for prolonged periods of time, this type of FES-mediated protocol facilitates functional reorganization and retraining of intact parts of the of central nervous system and allows them to take over the function of the damaged part of the central nervous system. As the individual continues to improve the voluntary function then the volitional-related sensory feedback from the stimulated muscles and arm further contributes to this retraining process. This is possible due to the distributed nature of the central nervous system and the fact that various parts of the brain are responsible for processing similar tasks. For example, motor tasks are typically associated with motor and pre-motor cortex activity. However, the motor tasks are also processed in the occipital lobe. Therefore, FES-mediated protocol is allowing the central nervous system to access such distributed networks and used them to help patient relearn new motor tasks, lost due to injury or disease of the central nervous system.

The present exemplary FES-mediated study may confirm that the FES-mediated protocol can be used to improve the upper limb functions in chronic stroke individuals. Furthermore, as this type of protocol may be effective in individuals with severe upper limb impairment, it is very likely that it is effective in individuals with less severe upper limb disability. The exemplary study investigated on weekly basis how the H-reflex and the EMGs of various muscles changed over time due to FES-mediated protocol. The key finding is that the muscles that were paralyzed prior to the study became active and were under voluntary control of the individual after the FES-mediated protocol. Furthermore, the H-reflex decreased almost 50% after the FES-mediated protocol was completed suggesting a significant reduction in muscle tone and/or spasticity as a result of this exemplary FES-mediated protocol. It would be appreciated that example embodiments may be applied to a variety of pulse generating circuits. For example, some pulse generating circuits are described in PCT application publication number WO2011/150502 entitled FUNCTIONAL ELECTRICAL STIMULATION DEVICE AND SYSTEM, AND USER THEREOF, filed Jun. 2, 2011, having a common co-inventor as the present application, the contents of which are hereby incorporated by reference. Such circuits may be programmed in accordance with at least some of the presently described example embodiments.

Some example embodiments may be applied to a "matrix-type electrode" as would be understood in the art. For example, a single output channel can be used to stimulate more than one point of contact on the skin, using a matrix of contact points. These points can be programmed or controlled in a number of ways, as appropriate.

It would be appreciated that the described FES systems may differ from some traditional fixed voltage systems which do not consider any desired steady state current value. Further, the described FES systems may differ from traditional current controlled systems which attempt to generate a rectangular current pulse, or attempt to dampen the current spike, or may merely measure the current until a total charge desired is reached.

Another example application of at least some example embodiments is for the rehabilitating, treating, retraining, and/or otherwise improving upper extremity mobility and control in persons having impaired or disabled upper extremities due to stroke or spinal cord injury, including stimulation of the lumbricalis muscles. An example of such a system and method is described in PCT application publication number WO 2014/000107 filed Jun. 26, 2013, having a common co-inventor as the present application, the contents of which are hereby incorporated by reference.

At least one example embodiment recognizes that there can be biological cross-talk between electrode leads in close proximity, such as when stimulating a group of close muscles such as the lumbricalis muscles. For example, if a spike in current of one electrode lead causes biological cross talk during the steady state current of another one of the electrode leads, this can affect the measurement of the signal levels which are taken during the steady state current of the another one of the electrode leads.

In an example embodiment, there is provided electrical stimulation system for providing pulse stimulation to a plurality of areas of a living body by way of a plurality of electrode leads each applied to one of the respective areas, each of the areas including an associated resistance element and an associated capacitance element. The system includes a plurality of pulse generating circuits each having a controllable output voltage to generate constant voltage pulses to one or more of the electrode leads, wherein the corresponding current signal of each constant voltage pulse includes an exponential decay to a steady state current value. At least one controller is configured to determine a specified target steady state current value to be applied to each area, estimate the associated resistance element of each area, control the pulse generating circuits to generate a constant voltage pulse to the electrode leads at a calculated voltage level which achieves the specified steady state current value to the area, and control a spike of one of the current signals for one of the electrode leads so as to be outside the steady-state current of another one of the electrode leads so as to allow accurate measurement of the steady-state current of the another one of the electrode leads.

In another example embodiment, there is provided electrical stimulation system for providing pulse stimulation to a plurality of areas of a living body by way of a plurality of electrode leads each applied to one of the respective areas, each of the areas including an associated resistance element and an associated capacitance element. The system includes a plurality of pulse generating circuits each having a controllable output voltage to generate constant voltage pulses to one or more of the electrode leads, wherein the corresponding current signal of each constant voltage pulse includes an exponential decay to a steady state current value. At least one controller is configured to estimate the associated resistance element of each area, control the pulse generating circuits to generate a constant voltage pulse to the electrode leads at a specified voltage level based on the measured steady-state current value, and control a spike of one of the current signals for one of the electrode leads so as to be outside the steady-state current of another one of the electrode leads so as to allow accurate measurement of the steady-state current of the another one of the electrode leads.

In an example embodiment, each constant voltage pulse from the respective pulse generating circuits for all of the electrode leads is controlled to pulse simultaneously (e.g. rise time starting position is substantially the same). In another example embodiment, the controller controls a spike of one of the current signals for one of the electrode leads so as to be within the exponential decay of another one of the electrode leads, so long as the spike is within a buffered time before the steady state of the another one of the electrode leads. This type of system contrasts with having to fire each pulse one-by-one, for example.

In an example embodiment, at least some of the plurality of areas are relatively located at a distance there between so as to cause biological cross-talk between two of the respective areas of the body where the respective electrode leads are located.

In an example embodiment, to reduce or eliminate the effects of biological cross-talk the current spike to at least one of the electrodes is controlled by applying a phase control, a delay control, or a compensating circuit, to at least one of the current signals for the respective electrode lead. Adjustment and calibration of each of the pulse generators in this manner may be performed prior to starting the present treatment protocol.

At least some example embodiments can be applied to other electrical stimulation systems. For example, a pacemaker or defibrillator may be configured to provide electrical stimulation to the heart in a controlled manner. Other example electrical stimulation system can be applied to neural stimulation for the brain, to assist in facilitating neural pathways, for example. Such a system, when configured with the electrical stimulation systems described herein, may include a controller configured to determine a specified target steady state current value to be applied to the area, and control the pulse generating circuit to generate a constant voltage pulse to the one or more electrode leads at a calculated voltage level which achieves the specified target steady state current value to the area. Each generated constant voltage pulse can include a faster rise time resulting in a lower required specified target steady state current than when compared to a constant voltage pulse having a slower rise time requiring a higher required specified target steady state current. This, for example, can save the amount of power consumed or total energy required to be provided by the source (e.g. limited lifetime battery). In another example embodiment, at least one electrode lead, and/or a portable battery, are implanted inside of the patient. Accordingly, reduction of power consumption can lead to improved patient comfort, longer use of the battery, and less surgery time required for replacing of the battery.

The example embodiments use constant voltage pulses which are in contrast to, and not the same as, a pulse generator which generates a rectangular constant current pulse. In a constant current pulse system, the current does eventually reach a desired steady state current value, but such systems can suffer from slow rise times due to the capacitance of the skin and other elements, for example. Also, such conventional systems do not have an initial inrush of current and can require a higher steady state current value when compared to the systems as described in at least some example embodiments.

While some of the embodiments are described in terms of methods, a person of ordinary skill in the art will understand that present embodiments are also directed to various apparatus including components for performing at least some of the aspects and features of the described methods, be it by way of hardware components, software or any combination of the two, or in any other manner. Moreover, an article of manufacture for use with the apparatus, such as a pre-recorded storage device or other similar non-transitory computer readable medium including program instructions recorded thereon, or a computer data signal carrying computer readable program instructions may direct an apparatus to facilitate the practice of the described methods. It is understood that such apparatus, articles of manufacture, and computer data signals also come within the scope of the present embodiments.

While some of the above examples have been described as occurring in a particular order, it will be appreciated to persons skilled in the art that some of the steps or processes may be performed in a different order provided that the result of the changed order of any given step will not prevent or impair the occurrence of subsequent steps. Furthermore, some of the steps described above may be removed or combined in other embodiments, and some of the steps described above may be separated into a number of sub-steps in other embodiments. Even further, some or all of the steps of the method may be repeated, as necessary. Elements described as methods or steps similarly apply to systems or subcomponents, and vice-versa.

The term "computer readable medium" as used herein includes any medium which can store instructions, program steps, or the like, for use by or execution by a computer or other computing device including, but not limited to: magnetic media, such as a diskette, a disk drive, a magnetic drum, a magneto-optical disk, a magnetic tape, a magnetic core memory, or the like; electronic storage, such as a random access memory (RAM) of any type including static RAM, dynamic RAM, synchronous dynamic RAM (SDRAM), a read-only memory (ROM), a programmable-read-only memory of any type including PROM, EPROM, EEPROM, FLASH, EAROM, a so-called "solid state disk", other electronic storage of any type including a charge-coupled device (CCD), or magnetic bubble memory, a portable electronic data-carrying card of any type including COMPACT FLASH, SECURE DIGITAL (SD-CARD), MEMORY STICK, and the like; and optical media such as a Compact Disc (CD), Digital Versatile Disc (DVD) or BLU-RAY Disc.

It should be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical or electrical connections or couplings. Furthermore, the specific mechanical or electrical configurations illustrated in the drawings are intended to exemplify embodiments of the disclosure. However, other alternative mechanical or electrical configurations are possible which are considered to be within the teachings of the present disclosure. Furthermore, unless otherwise indicated, the term "or" is to be considered inclusive.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art having the benefit of the present disclosure, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole.

The invention claimed is:

1. An electrical stimulation system for providing pulse stimulation to an area of a living body by way of one or more electrode leads applied to the area, the area including an associated resistance element and an associated capacitance element, comprising:
    a pulse generating circuit having a controllable output voltage to generate constant voltage pulses to the one or more electrode leads, wherein the corresponding current signal of each constant voltage pulse includes a spike in current followed by an exponential decay to a steady state current value;
    a controller configured to:
    estimate the associated resistance element of the area,
    determine a specified target steady state current value to be applied to the area, and
    control the pulse generating circuit to generate a constant voltage pulse to the one or more electrode leads at a calculated voltage level which achieves the specified target steady state current value to the area.

2. The electrical stimulation system as claimed in claim 1, wherein the calculated voltage level is calculated without consideration of a value of the associated capacitance element.

3. The electrical stimulation system as claimed in claim 1, wherein the controller is further configured to determine the associated resistance element of the area.

4. The electrical stimulation system as claimed in claim 3, wherein the controller is further configured to initially estimate the associated resistance element by applying one or more sub-threshold pulses to the area from the pulse generating circuit.

5. The electrical stimulation system as claimed in claim 1, further comprising a signal detector configured to detect signal parameters associated with the area of the living body, wherein the associated resistance element is determined from at least the detected signal parameters.

6. The electrical stimulation system as claimed in claim 1, wherein said estimating of the associated resistance element is performed by measuring the steady-state current during at least one of the pulses.

7. The electrical stimulation system as claimed in claim 1, wherein said determining the specified target steady state current value includes receiving the specified target steady state current value from a computer device, a user interface device, or from a memory.

8. The electrical stimulation system as claimed in claim 1, wherein the controller is further configured to:
  determine a next specified target steady state current value to be applied to the area; and
  control the pulse generating circuit to generate a next constant voltage pulse to the one or more electrode leads at a next calculated voltage level which achieves the next specified target steady state current value to the area.

9. The electrical stimulation system as claimed in claim 8, wherein the next calculated voltage level is calculated based on consideration of any determined changes to the associated resistance element of the area.

10. The electrical stimulation system as claimed in claim 1, wherein the constant voltage pulses provide sequential bipolar pulse stimulation comprising a pulse sequence including a positive constant voltage pulse and a negative constant voltage pulse through the area by way of the one or more electrode leads.

11. The electrical stimulation system as claimed in claim 10, wherein an amplitude and pulse width of the positive pulse and the negative pulse are controlled to be charge balanced during the pulse sequence.

12. The electrical stimulation system as claimed in claim 1, wherein a rise time of the spike in current is predominantly dictated by a switching speed of switches.

13. The electrical stimulation system as claimed in claim 1, further comprising a selectively activatable signal path from the switching circuit which is an alternate signal path from the area to selectively discharge any charge from the substantially constant voltage supply between pulses.

14. The electrical stimulation system as claimed in claim 1, wherein the electrical stimulation system comprises a functional electrical stimulation system.

15. The electrical stimulation system as claimed in claim 1, further comprising a plurality of pulse generating circuits including the pulse generating circuit, a plurality of electrodes including the one or more electrode leads, wherein the electrode leads are each applied to a respective plurality of areas including the area, wherein at least two of the plurality of areas are of a distance which causes biological cross-talk between respective electrode leads, wherein the controller is further configured to control the spike of one of the current signals for one of the electrode leads so as to be outside the steady-state current of another one of the electrode leads so as to allow accurate measurement of the steady-state current of the another one of the electrode leads.

16. The electrical stimulation system as claimed in claim 15, wherein each constant voltage pulse of each of the electrode leads are all activated substantially simultaneously.

17. The electrical stimulation system as claimed in claim 1, wherein each constant voltage pulse has a rise time of 50 nanoseconds or less.

18. The electrical stimulation system as claimed in claim 1, wherein each constant voltage pulse has a rise time of 20 nanoseconds or less.

19. A method for controlling an electrical stimulation system for providing pulse stimulation to an area of a living body by way of one or more electrode leads applied to the area, the area including an associated resistance element and an associated capacitance element, wherein the electrical stimulation system includes a pulse generating circuit having a controllable output voltage to generate constant voltage pulses to the one or more electrode leads, wherein the corresponding current signal of each constant voltage pulse includes a spike in current followed by an exponential decay to a steady state current value, the method comprising:
  estimating the associated resistance element of the area;
  determining a specified target steady state current value to be applied to the area; and
  controlling the pulse generating circuit to generate a constant voltage pulse to the one or more electrode leads at a calculated voltage level which achieves the specified target steady state current value to the area.

20. A controller for controlling an electrical stimulation system for providing pulse stimulation to an area of a living body by way of one or more electrode leads applied to the area, the area including an associated resistance element and an associated capacitance element, wherein the electrical stimulation system includes a pulse generating circuit having a controllable output voltage to generate constant voltage pulses to the one or more electrode leads, wherein the corresponding current signal of each constant voltage pulse includes a spike in current followed by an exponential decay to a steady state current value, the controller being configured to:
  estimate the associated resistance element of the area;
  determine a specified target steady state current value to be applied to the area; and
  control the pulse generating circuit to generate a constant voltage pulse to the one or more electrode leads at a calculated voltage level which achieves the specified target steady state current value to the area.

21. An electrical stimulation system for providing pulse stimulation to a plurality of areas of a living body by way of a plurality of electrode leads each applied to one of the respective areas, each of the areas including an associated resistance element and an associated capacitance element, at least two of the plurality of areas are of a distance which causes biological cross-talk between respective electrode leads, the system comprising:
  a plurality of pulse generating circuits each having a controllable output voltage to generate constant voltage pulses to one or more of the electrode leads, wherein the corresponding current signal of each constant voltage pulse includes an exponential decay to a steady state current value; and
  at least one controller is configured to:
  estimate the associated resistance element of each area,
  control the pulse generating circuits to generate a constant voltage pulse to each of the electrode leads at a specified voltage level based on the measured steady-state current value, and
  control a spike of one of the current signals for one of the electrode leads so as to be outside the steady-state current of another one of the electrode leads to allow accurate measurement of the steady-state current of the another one of the electrode leads.

* * * * *